United States Patent
Scheidt et al.

(10) Patent No.: US 9,840,487 B2
(45) Date of Patent: Dec. 12, 2017

(54) CATALYTIC ENANTIOSELECTIVE SYNTHESIS OF 2-ARYL CHROMENES AND RELATED PHOSPHORAMIDITE LIGANDS AND CATALYST COMPOUNDS

(71) Applicant: Northwestern University, Evanston, IL (US)

(72) Inventors: Karl A. Scheidt, Evanston, IL (US); Bi-Shun Zeng, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/487,592

(22) Filed: Apr. 14, 2017

(65) Prior Publication Data

US 2017/0217919 A1    Aug. 3, 2017

Related U.S. Application Data

(62) Division of application No. 15/095,855, filed on Apr. 11, 2016, now Pat. No. 9,624,190, which is a division of application No. 14/701,170, filed on Apr. 30, 2015, now Pat. No. 9,309,217.

(60) Provisional application No. 61/987,308, filed on May 1, 2014.

(51) Int. Cl.
*C07D 311/60*    (2006.01)

(52) U.S. Cl.
CPC .................. *C07D 311/60* (2013.01)

(58) Field of Classification Search
CPC ... C07D 311/60; C07D 311/32; C07D 311/62; C07B 53/00; C07F 9/591; C07F 9/65515; C07F 9/657154
See application file for complete search history.

(56) References Cited

PUBLICATIONS

Rueping et al., "Chiral Organic Contact Ion Pairs in Metal-Free Catalytic Asymmetric Allylic Substitutions", J. Am. Chem. Soc., 133, 3732-3735 (2011).
Hardouin, C. et al., "Enantioselective synthesis of chromenes", Tetrahedron Lett., 2003, 44, 435-437.
Moquist, P.N. et al., "Enantioselective Addition of Boronates to Chromene Acetals Catalyzed by a Chiral Bronsted Acid/Lewis Acid System", Angew. Chem. Int. Ed., 2010, 49, 7096-7100.
Barbaro, P. et al., "Chiral P,S-Ligands Based on Beta-D-Thioglucose Tetraacetate. Palladium(II) Complexes and Allylic Alkylation", Organometallics, 1996, 15, 1879-1888.
Alexakis, A. et al., "Synthesis and Application of Chiral Phosphorus Ligands Derived from Taddol for the Asymmetric Conjugate Addition of Diethyl Zinc to Enones", Eur. J. Org. Chem., 2000, 4011-4027.
He, H. et al., "Iridium-Catalyzed Asymmetric Allylic Etherification and Ring-Closing Metathesis Reaction for Enantioselective Synthesis of Chromene and 2,5-Dihydrobenzo [b]oxepine Derivatives", Adv. Synth. Catal., 2012, 354, 1084-1094.

*Primary Examiner* — Erich A Leeser
(74) *Attorney, Agent, or Firm* — Reinhart Boerner Van Deuren s.c.

(57) ABSTRACT

Methods to access 2-aryl chromene compounds via an asymmetric catalytic process.

2 Claims, 3 Drawing Sheets
(1 of 3 Drawing Sheet(s) Filed in Color)

Examples of biologically relevant 2-aryl-2H-chromenes anti-inflammatory
($IC_{50}$ = 11.6 umol/L)

(2S)-candenatenin E
(cancer cell cytotoxicity)

tyrosine kinase inhibitor
($IC_{50}$ = 12 nmol/l)

hilgartene (pesticide)

CATALYTIC ENANTIOSELECTIVE SYNTHESIS OF 2-ARYL CHROMENES AND RELATED PHOSPHORAMIDITE LIGANDS AND CATALYST COMPOUNDS

This application is a divisional of and claims priority to and the benefit of application Ser. No. 15/095,855 filed Apr. 11, 2016 and issued as U.S. Pat. No. 9,624,190 on Apr. 18, 2017, which was a divisional of and claimed priority to and the benefit of application Ser. No. 14/701,170 filed Apr. 30, 2015 and issued as U.S. Pat. No. 9,309,217 on Apr. 12, 2016, which claimed priority to and the benefit of application Ser. No. 61/987,308 filed May 1, 2014—each of which is incorporated herein by reference in its entirety.

This invention was made with government support under grant number P50 GM086145 awarded by the National Institutes of Health. The government has certain rights in the invention.

BACKGROUND OF THE INVENTION

Chromenes constitute a privileged class of structural motifs present in a myriad of natural products and medicinally important agents. Given the prevalence of this structural unit, there has been considerable interest in developing methods for the generation of the chromene skeleton. While procedures to access racemic 2-aryl-2H-chromenes are readily available, the difficulty in generating enantioselective variants is underscored by the scarcity of documented strategies to produce these bioactive structures. The construction of enantioenriched 2-aryl-2H-chromenes has been recently reported by You through a Ru-catalyzed ring-closing metathesis reaction of chiral allyl ethers and also by Schaus via the chiral Brønsted acid (CBA)/Lewis acid-catalyzed addition of aryl boronates to in situ formed pyrylium ions. In addition, Rueping has recently reported a CBA-catalyzed closure of allylic cations, but this innovative approach requires substitution at C4. (See, e.g., H. He, K. Y. Ye, Q. F. Wu, L. X. Dai and S. L. You, *Adv. Synth. Catal.*, 2012, 354, 1084-1094; C. Hardouin, L. Burgaud, A. Valleix and E. Doris, Tetrahedron Lett., 2003, 44, 435-437; P. N. Moquist, T. Kodama and S. E. Schaus, *Angew. Chem. Int. Ed.*, 2010, 49, 7096-7100; M. Rueping, U. Uria, M. Y. Lin and I. Atodiresei, *J. Am. Chem. Soc.*, 2011, 133, 3732-3735.)

SUMMARY OF THE INVENTION

In light of the foregoing, it is an object of the present invention to provide methods and/or catalytic systems for the enantioselective synthesis of 2-aryl chromene compounds, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to provide such a synthesis without prerequisite, limiting starting material substitution of the sort discussed above.

It can be another object of the present invention to provide a catalysis system and reagent alleviating undue concern over unwanted side reactions.

It can also be an object of the present invention, alone or in conjunction with one or more of the preceding objectives, to provide an enantioselective route to the preparation of a range of therapeutic compounds.

Other objects, features, benefits and advantages of the present invention will be apparent from this summary and the following descriptions of various preferred embodiments, and will be readily apparent to those skilled in the art having knowledge of enantioselective synthetic techniques. Such objects, features, benefits and advantages will be apparent from the above as taken into conjunction with the accompanying examples, data, figures and all reasonable inferences to be drawn therefrom, alone or with consideration of the references incorporated herein.

In part, the present invention can be directed to a method for asymmetric synthesis of a 2-aryl chromene compound. Such a method can comprise providing a reaction medium comprising an o-arylallyl-substituted phenoxy ester starting material of a formula

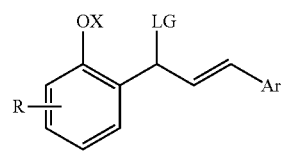

wherein X can be selected from alkylcarbonyl and alkylcarbonyl moieties, LG can be a leaving group selected from alkoxycarbonyl groups, R can be selected from H, halo, alkyl and alkoxy moieties, multiple moieties and combinations thereof and Ar can be a moiety selected from aryl and substituted aryl moieties, such aryl substituents as can be selected from halo, alkyl, alkoxy and nitro substituents, multiple such substituents and combinations thereof; introducing a palladium (II) catalyst precursor compound and a phosphoramidite ligand compound to such a reaction medium; reacting such a starting material with a base component to promote intramolecular cyclization of such a reacted starting material and provide an asymmetric 2-aryl chromene compound of a formula

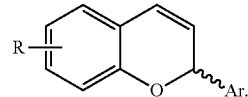

In certain non-limiting embodiments, such a phosphoramidite ligand compound can be of a formula

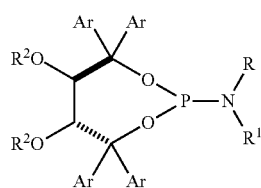

wherein R and $R^1$ can be independently selected from alkyl, phenyl, phenylalkyl and cycloalkyl moieties, and where R and $R^1$ can together provide a divalent alkylene moiety; each $R^2$ can be independently selected from methyl and ethyl moieties, and where the $R^2$ moieties together can provide a divalent moiety selected from alkylene and alkyl-substituted alkylene moieties; and each Ar can be independently selected from phenyl and substituted phenyl moieties. In certain such embodiments, each of R and $R^1$ can be a chiral $CH(CH_3)C_6H_5$ moiety. In certain other such embodiments, R and $R^1$ can together provide a divalent $(CH_2)_m$ moiety, wherein m can be an integer selected from 4-6.

Regardless, without limitation, each Ar can be an alkyl-substituted phenyl moiety. In certain embodiments, such a phosphoramidite ligand compound can be of a formula

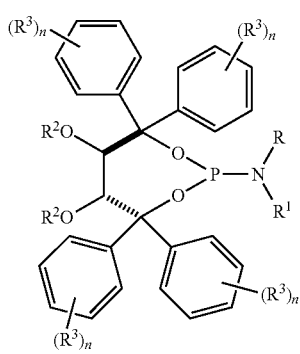

wherein each $R^3$ can be independently selected from methyl and ethyl moieties and combinations thereof, and each n can independently be an integer selected from 1-3. In certain such non-limiting embodiments, each $R^3$ can be ethyl and each n can be 2, to provide such a ligand compound with 3,5-diethyl substituted phenyl moieties.

With respect to an aforementioned ester starting material, such an Ar moiety can be selected from substituted phenyl and naphthyl moieties. In certain non-limiting embodiments, such a phenyl moiety can be substituted with one or more halo, alkyl, alkoxy, nitro and haloalkyl substituents, multiple such substituents and combinations thereof. Regardless, X can be selected from acetyl and benzoyl moieties, and LG can be selected from acetyloxy and benzoyloxy moieties. In certain such embodiments, X can be acetyl and LG can be acetyloxy, to provide a bis-acetate starting material. Irrespective of ester identity, chromene synthesis can proceed with a phosphoramidite ligand of the sort described above, wherein, for instance, R and $R^1$ can together provide a divalent $(CH_2)_m$ moiety, where m can be an integer selected from 4-6, and each Ar can be an alkylated phenyl moiety.

In part, the present invention can also be directed to a method of using intramolecular cyclization for enantioselective synthesis of a 2-aryl-2H-chromene compound. Such a method can comprise providing a reaction medium comprising an o-arylallyl-substituted bis-acetate compound of the sort described herein, a base component, a palladium (II) catalyst precursor compound and a chiral phosphoramidite ligand compound of the sort discussed above or illustrated elsewhere herein (e.g., without limitation, L3 or L4, below); and deacylating such a bis-acetate compound to promote intramolecular cyclization and C—O bond formation, to enantioselectively provide a compound of a formula

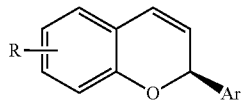

wherein R is selected from H, halo, alkyl and alkoxy moieties, and Ar is selected from phenyl, substituted phenyl and naphthyl moieties, whereby such a compound can have an enantiomeric ratio of greater than about 60:40 for said enantiomer.

In certain non-limiting embodiments, such a ligand compound can be of the sort described above and illustrated elsewhere herein. For instance, R and $R^1$ can together provide a divalent $(CH_2)_m$ moiety, wherein m is an integer selected from 4-6. Alternatively, R can be alkyl and $R^1$ can be cycloalkyl. Regardless of R/$R^1$ identity, each Ar can be an alkyl-substituted phenyl moiety. In certain embodiments, each Ar can be a dialkyl-substituted phenyl moiety, such as a 3,5-dimethyl- or a 3,5-diethyl-substituted phenyl moiety. Use of such ligand compounds in conjunction with the present method(s) can provide a 2-aryl-2H-chromene compound with an enantiomeric ratio of greater than about 90:10 for one enantiomer thereof.

In part, the present invention can also be directed to compositions comprising compounds of a formula

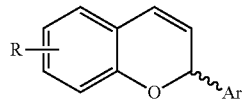

wherein R can be selected from H, halo, alkyl and alkoxy moieties, multiple such moieties and combinations thereof and Ar can be selected from phenyl and substituted phenyl moieties, such phenyl substituents as can be selected from halo, alkyl, alkoxy, nitro and haloalkyl substituents, multiple such substituents and combinations thereof, such a composition as can comprise at least about 70% an enantiomer of a formula

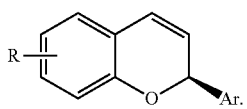

In certain non-limiting embodiments, such a moiety can be selected from methyl, methoxy, fluoro, chloro, nitro and dichlorosubstituted phenyl moieties, and such a composition can comprise at least about 90% of such an enantiomer.

Accordingly, the present invention can, in part, be directed to a ligand compound of a formula

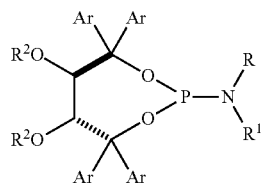

wherein R and $R^1$ can be independently selected from alkyl, phenyl, phenylalkyl and cycloalkyl moieties, and where R and $R^1$ can together provide a divalent alkylene moiety; each $R^2$ can be independently selected from methyl and ethyl moieties, and where the $R^2$ moieties together can provide a divalent moiety selected from alkylene and alkyl-substituted alkylene moieties; and each Ar can be independently selected from phenyl and substituted phenyl moieties. In certain such embodiments, each of R and $R^1$ can be a chiral $CH(CH_3)C_6H_5$ moiety. In certain other such embodiments, R and $R^1$ can together provide a divalent $(CH_2)_m$ moiety, wherein m can be an integer selected from 4-6. In various other non-limiting embodiments, R can be a methyl moiety and $R^1$ can be a cyclohexyl moiety, or R and $R^1$ can together provide a divalent $(CH_2)_5$ moiety; each $R^2$ can be a methyl moiety or each $R^2$ can together provide a divalent $C(CH_3)_2$ moiety; and each Ar can be independently selected from phenyl, methyl- and polymethyl-substituted phenyl, and ethyl and polyethyl-substituted phenyl moieties. As discussed below, such a ligand compound can be complexed, bound, coordinated or otherwise coupled to a palladium metal component. Such complexation and the like can provide a palladium catalyst of the sort described below and useful in conjunction with the synthetic method(s) of this invention.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 1. Schematic reaction design for 2-aryl-2H-chromenes, illustrating methods of this invention and, without limitation, representative compounds available therefrom. FIG. 2. Proposed reaction pathway. FIG. 3. Molecular structure of [Pd($\eta^3$-1,3-diphenylallyl) {(S,S)-L3g}]BF$_4$. ORTEP at 80% probability with hydrogen atoms and BF$_4$ omitted for clarity.

DETAILED DESCRIPTION OF CERTAIN EMBODIMENTS

By way of developing new approaches to construct pyran and related motifs, an investigation was begun relating to substrate/catalyst activation combinations to access chromenes via an asymmetric catalytic process. After extensive exploration with substrates such as 1 (not shown), easily accessed from chalcone precursors, the use of either organocatalysis or transition metal catalysis led to an invariable observation: compounds with unprotected ortho-substituted phenols were typically unstable and often underwent uncatalyzed cyclizations to racemic chromenes rapidly (eq 1).

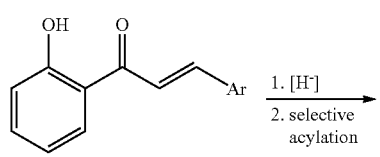

(1)

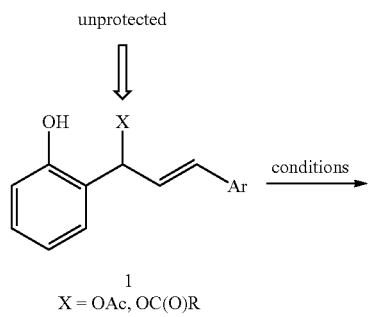

1
X = OAc, OC(O)R

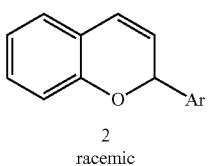

2
racemic

Figure 1:
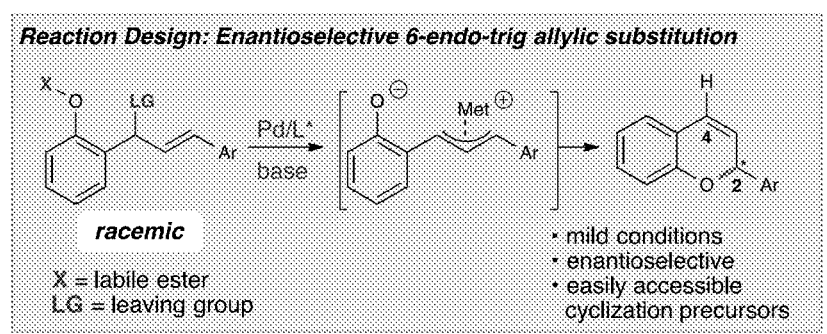
FIGS. 1-3.
Figure 1:
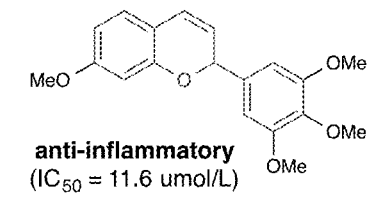
Figure 1:
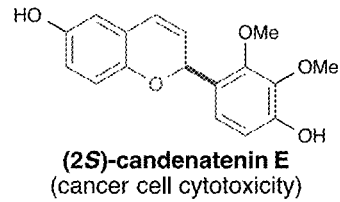
Figure 1:
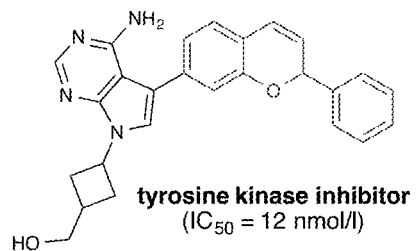
Figure 1:
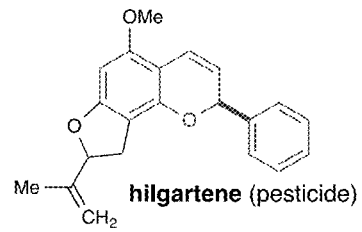

With this data in hand and the background reaction a concern, the following reaction design factors were considered: a) promote phenol formation during the course of the reaction, b) avoid any background reactions by activating an allylic system through a chiral metal complex or organocatalytic mechanism, and c) promote a 6-endo-trig type closure of the phenol/phenoxide with control of the absolute stereochemistry. Based on this logic, it was envisaged that 2-aryl-2H-chromenes could be constructed through a 6-endo-trig Pd-catalyzed asymmetric allylic substitution (FIG. 1). While Pd-catalyzed allylic alkylation is a prominent strategy for C—C and C-heteroatom bond formation, it is believed there are no reports of a general asymmetric 6-endo-trig variant.

This investigation began by combining bis-acetate 1a with potassium carbonate, a palladium source or catalyst precursor compound such as palladium dibenzylideneacetone, Pd$_2$(dba)$_3$, and a variety of phosphoramidite ligands. (Various other palladium sources can be used, as would be understood by those skilled in the art and made aware of this invention.) Although monodentate phosphoramidites are efficient chiral ligands in promoting various Pd-catalyzed reactions, their application in asymmetric allylic substitutions remains underdeveloped. Initial ligand screens included BINOL-, SIPHOS-, and TADDOL-derived phosphoramidites. Preliminary experiments with BINOL-derived ligand L1a provided chromene 2a in quantitative yield with an encouraging 69:31 enantiomeric ratio (Table 1, entry 1). Unfortunately, modification of the amine constituent to piperidine, dimethylamine, 1-phenylethylamine (results not shown) or bis[(S)-1-phenethyl]amine (entry 2), was detrimental to both the conversion and enantioselectivity. The modification of the ligand backbone to SIPHOS-derived ligand ($R_a$,R,R)-L2 and TADDOL-derived ligand L3a resulted in significantly improved levels of enantioselectivity (entries 3 and 5, respectively). Interestingly, the diastereomer ($S_a$,R,R)-L2 (entry 4) afforded racemic chromene product, suggesting a mismatch of stereogenic elements.

TABLE 1

Optimization of reaction conditions.

| entry | ligand | Ar | NRR$^1$ | time$^a$ | er$^b$ |
|---|---|---|---|---|---|
| 1 | L1a | — | N(i-Pr)$_2$ | 2 h | 69:31 |
| 2 | L1b | — | N((S)—CH(Me)(Ph))$_2$ | 21 h | 57:43 |
| 3 | ($R_a$, R, R)-L2 | — | — | 1 d | 79:21 |

TABLE 1-continued

Optimization of reaction conditions.

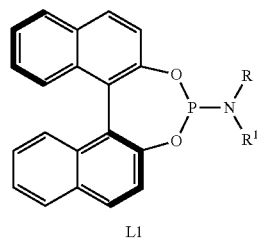
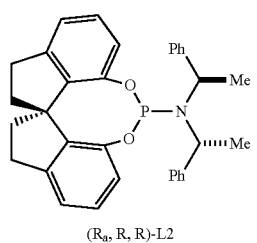

| entry | ligand | Ar | NRR¹ | time$^a$ | er$^b$ |
| --- | --- | --- | --- | --- | --- |
| 4 | ($S_a$, R, R)-L2 | — | — | 1 d | 50:50 |
| 5 | L3a | Ph | N((S)—CH(Me)(Ph))$_2$ | 12 h | 74:26 |
| 6 | L3b | Ph | N(Me)$_2$ | 2 h | 60:40 |
| 7 | L3c | Ph | N(i-Pr)$_2$ | 4 h | 65:35 |
| 8 | L3d | Ph | N(CH$_2$)$_5$ | 2 h | 82:18 |
| 9 | L4 | Ph | N(CH$_2$)$_5$ | 3 h | 53:47 |
| 10 | L3e | 2-Me-C$_6$H$_4$ | N(CH$_2$)$_5$ | 12 h | 85:15 |
| 11 | L3f | 3-Me-C$_6$H$_4$ | N(CH$_2$)$_5$ | 19 h | 90:10 |
| 12 | L3g | 3,5-Me-C$_6$H$_3$ | N(CH$_2$)$_5$ | 38 h | 93:7 |
| 13 | L3h | 3,5-Me-C$_6$H$_3$ | N(CH$_2$)$_4$ | 2 d | 71:29 |
| 14 | L3i | 3,5-Me-C$_6$H$_3$ | N(CH$_2$)$_6$ | 2 d | 93:7 |
| 15 | L3j | 3,5-Me-C$_6$H$_3$ | N(Me)(Cy) | 19 h | 93:7 |
| 16 | L3k | 3,5-Et-C$_6$H$_3$ | N(CH$_2$)$_5$ | 19 h | 95:5 |

$^a$Time to reach 100% conversion as measured by ¹H NMR (500 MHz). Longer reactions did not provide side products.
$^b$Enantiomeric ratio determined by HPLC.

Due to the shortened reaction time with ligand L3a compared to L2 and the opportunity to rapidly evaluate a wide range of TADDOL-derived ligands, efforts were focused on the optimization of this ligand backbone. A variety of N-substituents were evaluated, including achiral and sterically less demanding amine moieties (entry 6-8). In comparison to ligand L3a, other acyclic amines such as dimethylamine (entry 6) and diisopropyl amine (entry 7) resulted in decreased enantioselectivity, while replacement with the more rigid piperidinyl substituent afforded chromene 2a with improved selectivity (82:18 er, entry 8). To understand the effects of ligand rigidity on engendering enantioselection, the isopropylidene acetal of L3 was substituted with an acyclic dimethyl ether motif. With the less rigid L4 as the ligand, chromene 2a was furnished with low enantioselectivity (entry 9).

Another point of variation of the TADDOL-derived ligands lies in the substitution about the arene rings. The examination of various aryl-substituted TADDOL ligands (entry 10-12) revealed that enantioselectivity can be enhanced through the placement and positioning of methyl groups on the aryl ring, culminating in a 93:7 er attained for ligand L3g (entry 12). The effects of the nitrogen substituent were then revisited. Interestingly, the replacement of the piperidine with a pyrrolidine resulted in a significant decrease in enantioselectivity (entry 13), while incorporation of a 7-membered azepane maintained the previously observed 93:7 er (entry 14). Efforts to increase enantioselectivity by utilizing acyclic amines were ineffective (entry 15). Finally, the incorporation of ethyl groups at the 3- and 5-position of the aryl ring was explored. It was interesting to find that with this ligand (L3k), chromene 2a was obtained in 71% isolated yield with 95:5 er (entry 16).

TABLE 2

Substrate scope[a].

Reaction scheme: 1a-p → 2a-p; conditions: 2 mol % Pd$_2$(dba)$_3$, 8 mol % L3k, 1 equiv K$_2$CO$_3$, MeOH/H$_2$O (1:1), CH$_2$Cl$_2$, 23° C. Starting material bears OAc, OAc, R substituents and styrenyl Ar group; product is 2-aryl-2H-chromene.

- 2a: 71%, 95:5 er
- 2b Ar = 1-naph: 71%, 94:6 er
- 2c Ar = 2-naph: 87%, 91:9 er
- 2d (o-Me): 72%, 92:8 er
- 2e (p-Me): 73%, 93:7 er
- 2f (m-OMe): 78%, 94:6 er
- 2g (o-F): 75%, 91:9 er
- 2h (p-F): 84%, 95:5 er
- 2i (m-Cl): 81%, 93:7 er
- 2j (p-CF$_3$): 81%, 83:17 er
- 2k (3,4-diCl): 74%, 90:10 er
- 2l (m-NO$_2$): 71%, 92:8 er
- 2m (7-F): 69%, 90:10 er
- 2n (6-F): 72%, 97:3 er
- 2o (6-OMe): 80%, 86:14 er
- 2p (8-Me): 73%, 85:15 er

[a]See Supporting Information for details. Yield of isolated product after chromatography. Enantiomeric ratio determined by HPLC analysis.

With selective conditions developed, several bis-acetate substrates were evaluated (Table 2). The high levels of enantioselectivity observed for 2a were maintained with extended aromatic moieties (2b and 2c). Electron-donating groups on the styrenyl component were also well-tolerated, with methyl substitution in the ortho- or para-positions (2d and 2e, respectively) affording the chromene products in good yield and excellent enantioselectivity. The electron-rich 3-methoxy substituted cyclization precursor also performed well in this reaction, generating chromene 2f (78%, 94:6 er).

The incorporation of electron-withdrawing (2g-2l) substituents around the pendant aromatic ring was also accommodated. Furthermore, it was found that the electronegative fluorine substituent can occupy various positions while maintaining high er. The erosion of enantioselectivity was observed with substrates possessing a trifluoromethyl, dichloro, or the strongly electronegative nitro group (2j-2l), but a fluorine substituent was tolerated at various positions (2m-n) with respect to the incipient phenoxide moiety. The electron-donating methoxy group was also accommodated, albeit with a slight decrease in enantioselectivity (2o). Additionally, the preparation of chromene 2p indicates that this system tolerates moderate substitution adjacent to the phenoxide.

Figure 2:
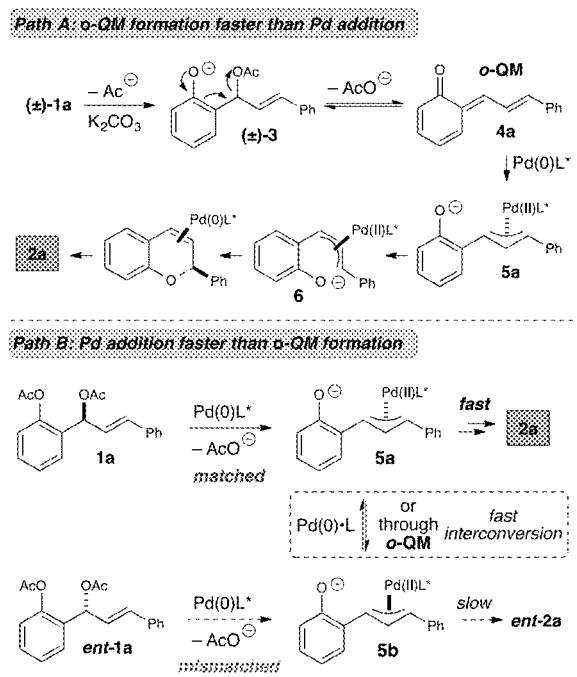
Figure 3:
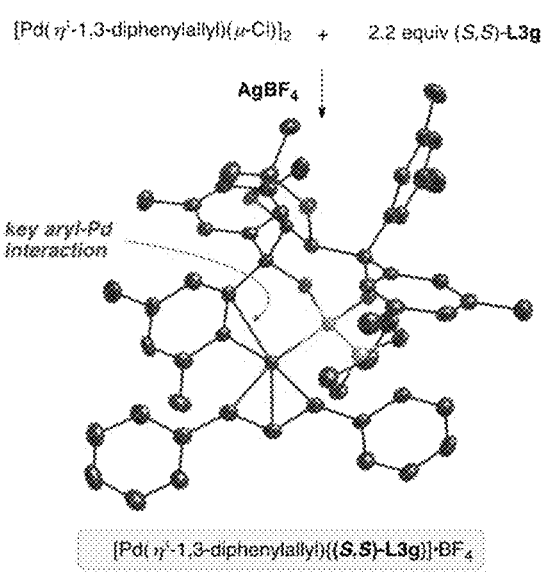

Without limitation to any one theory or mode of operation, the complete conversion of racemic substrates 1 to the enantioenriched chromenes indicates that a dynamic kinetic asymmetric transformation (DYKAT) might be operative. Since both enantiomers of the starting material must go through a common intermediate, and the unsymmetrical 1,3-disubstituted allyl substrate precludes racemization through a palladium π-σ-π allyl rearrangement, the generation of an achiral ortho-quinone methide intermediate (4) can be proposed to account for the high levels of enantioselectivity observed for the chromene products (FIG. 2).

Current understanding of the reaction contemplates subjection of either enantiomer of 1a to potassium carbonate and methanol, which rapidly produces the nucleophilic phenoxide in situ (±3, Path A). This deacylation promotes ejection of the secondary acetate to form the achiral trans o-quinone methide (o-QM, 4a). A subsequent coordination and addition of the chiral palladium complex generates the π allyl intermediate (5a) which undergoes intramolecular attack of the proximal phenoxide after bond rotation to achieve the proper conformation (6). For this pathway, the rate of o-QM formation is faster than addition of the palladium.ligand complex to ±3 (or ±1). If this is not the case, then an alternative potential pathway could be operative (Path B). This process involves the generation of diasteromeric π allyl palladium complexes (5a or 5b) from each enantiomer of 3. While one of these additions would be the "matched" case, a rapid interconversion between the diasteromeric intermediates is required so the "mismatched" complex undergoes smooth conversion to the observed enantiomer (2a) vs. the undesired isomer (ent-2a). Possible mechanisms for this involve generation of the achiral o-QM or direct addition of the palladium complex. Again, without limitation, Path A is currently favoured due to the lack of observed correlation between enantioselectivity and catalyst concentration, which disfavors Path B. Additionally, the use of bis-benzoylated substrates (vs. acetates) proceeds at the approximately the same rate with the similar levels of er and yield.

It was undertaken to further elucidate the structure of the Pd(II)-L3k complex and its interaction with the bis-acetate substrate 1a. Toward that end, X-ray quality crystals of the related Pd(II) complex has been solved using ligand L3g in conjunction with 1,3-diphenyl allyl acetate as a substrate surrogate incapable of closure (FIG. 2). The structure shows that the phosphoramidite ligand L3g is coordinated to the Pd(II) center through its phosphorus center and a single aryl ring. This η²-arene stabilization results in the observed 1:1 phosphoramidite-Pd(II) complex and supports mono-coordination of a bulky ligand to the palladium. The conversion and enantiomeric ratio of the chromene product, as well as reaction rate, remained unperturbed upon a reduction in ligand loading from 8 to 4 mol % (i.e., 2:1 to 1:1 phosphoramidite:Pd).

To highlight the potential of this new approach, it was thought to undertake the synthesis of catechin 8, which has demonstrated anti-staphylococcal activity due to the ability to reverse methicillin resistance in strains of drug resistant Staph. *aureus*. Interestingly, this catechin analog has increased activity compared to the parent (−)-epicatechin gallate, which bears additional hydroxyl groups on the catechin core (7). The regioselective hydroboration of 2a delivered chromanol 7 with 9:1 dr favoring the desired anti relationship. The esterification of chromanol 7 with tri-OBn gallic acid chloride followed by hydrogenolysis afforded 8 in 65% yield over the two steps. In a second vignette, the synthesis of hydroxyflavanone 10 was accomplished. The racemate of this compound exhibited promising levels of inhibition of *M. tuberculosis* H37Rv. Application of the present methodology allows access to enantioenriched 10 and could facilitate improved structure-activity relationship (SAR) studies. A cis-dihydroxylation of chromene 2i (94:6 er) using 3 mol % OsO₄ and NMO provided 2,3-trans-3,4-phenylchromandiol (5.6:1 dr). A recrystallization of the mixture provided a single diastereomer with >99:1 er. The exposure of diol 9 to MnO₂ resulted in the desired benzylic oxidation, without epimerization at C-3, to furnish 10 in 59% yield (Scheme 1).

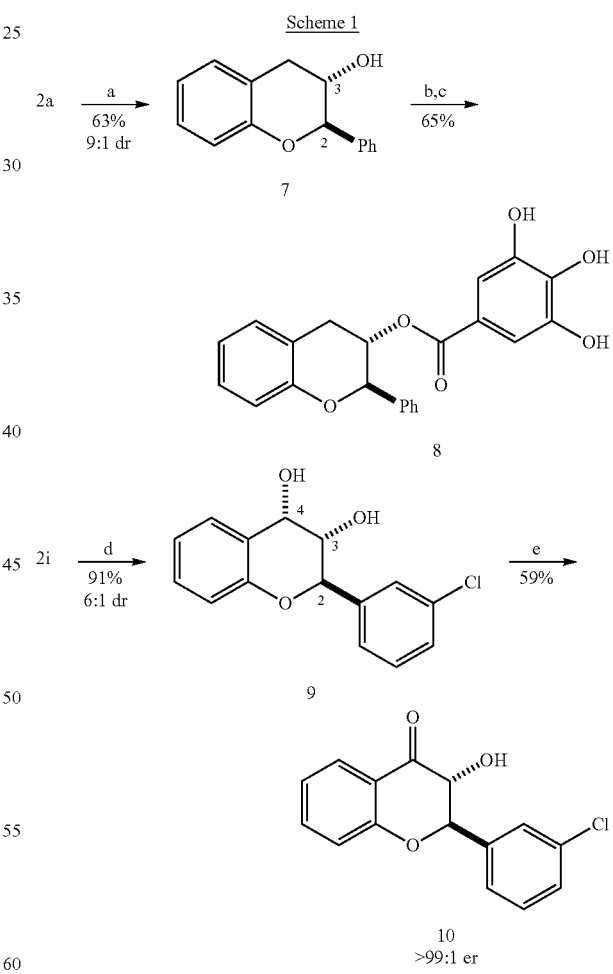

Transformation to bioactive flavonoids. Reagents and conditions:
(a) i. BH₃⊕THF, ii. H₂O₂, NaOH;
(b) tri-OBn galloyl chloride, DMAP, Et₃N, CH₂Cl₂;
(c) H₂, 10% Pd/C, EtOAc;
(d) 3 mol % OsO₄, 4-methylmorpholine 4-oxide, t-BuOH, H₂O;
(e) MnO₂, CH₂Cl₂.

As demonstrated, the present invention provides a catalytic enantioselective method for the synthesis of 2-aryl-2H-chromenes. A ligand structure-selectivity relationship study resulted in the development of a novel monodentate phosphoramidite system that enabled the synthesis of these privileged heterocycles with high yield and enantioselectivity. Crystallographic analysis provides mechanistic support that aryl ligand-metal interactions provide unanticipated additional rigidity in competing diastereomeric transition states which promotes the high levels of enantioselectivity for the newly formed C—O bond.

Examples of the Invention

The following non-limiting examples and data illustrate various aspects and features relating to the methods and compounds of the present invention, including the preparation of various 2-aryl chromene compounds, as are available through the synthetic methodologies described herein. In comparison with the prior art, the present methods and compounds provide results and data which are surprising, unexpected and contrary thereto. While the utility of this invention is illustrated through the use of several arylallyl-substituted phenoxy ester starting materials and phosphoramidite catalyst compounds and respective substituents thereon, it will be understood by those skilled in the art that comparable results are obtainable with various other starting materials, catalyst compounds and respective substituents, as are commensurate with the scope of this invention.

General Information

All reactions were carried out under a nitrogen atmosphere in flame-dried glassware with magnetic stirring. THF, toluene, and dichloromethane were purified by passage through a bed of activated alumina. Reagents were purified prior to use unless otherwise stated following the guidelines of Perrin and Armarego. (D. D. Perrin and W. L. F. Armarego, *Purification of Laboratory Chemicals;* 3rd Ed., Pergamon Press, Oxford. 1988.) Purification of reaction products was carried out by flash chromatography using EM Reagent or Silicycle silica gel 60 (230-400 mesh). Analytical thin layer chromatography was performed on EM Reagent 0.25 mm silica gel 60-F plates. Visualization was accomplished with UV light and ceric ammonium nitrate stain or potassium permanganate stain followed by heating. Infrared spectra were recorded on a Bruker Tensor 37 FT-IR spectrometer. $^1$H-NMR spectra were recorded on a Bruker Avance 500 MHz w/ direct cryoprobe (500 MHz) spectrometer and are reported in ppm using solvent as an internal standard (CDCl$_3$ at 7.26 ppm). Data are reported as (ap=apparent, s=singlet, d=doublet, t=triplet, q=quartet, m=multiplet, b=broad; coupling constant(s) in Hz; integration). Proton-decoupled $^{13}$C-NMR spectra were recorded on a Bruker Avance 500 MHz w/ direct cryoprobe (125 MHz) spectrometer and are reported in ppm using solvent as an internal standard (CDCl$_3$ at 77.2 ppm). Mass spectra data were obtained on a Waters Acquity Single Quadrupole ESI Spectrometer, Micromass Quadro II Spectrometer and Agilent 7890 GC-TOF.

Benzaldehyde and 2'-hydroxyacetophenone derivatives were obtained from commercial sources (Sigma Aldrich, Oakwood). Chalcones and phosphoramidites were prepared according to published procedures. (See, L. D. Chiaradia, A. Mascarello, M. Purificacao, J. Vernal, M. N. S. Cordeiro, M. E. Zenteno, A. Villarino, R. J. Nunes, R. A. Yunes, and H. Terenzi, *Bioorg. Med. Chem. Lett.,* 2008, 18, 6227-6230; and A. Alexakis, J. Burton, J. Vastra, C. Benhaim, X. Fournioux, A. van den Heuvel, J. M. Leveque, F. Maze, and S. Rosset, *Eur. J. Org. Chem.,* 2000, 4011-4027, respectively.)

Example 1

General Procedure for the Synthesis of 2'-Hydroxychalcone Derivatives

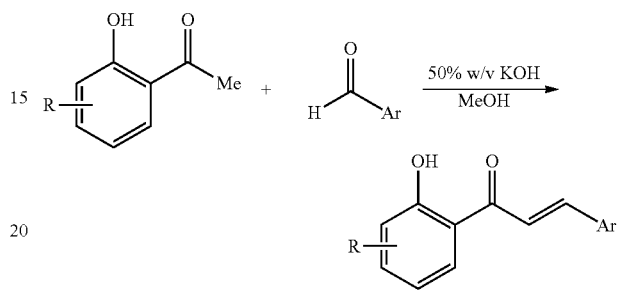

2'-Hydroxychalcones were prepared using a modified literature procedure. (L. D. Chiaradia, A. Mascarello, M. Purificacao, J. Vernal, M. N. S. Cordeiro, M. E. Zenteno, A. Villarino, R. J. Nunes, R. A. Yunes, and H. Terenzi, *Bioorg. Med. Chem. Lett.,* 2008, 18, 6227-6230.) Into a round bottom flask equipped with magnetic stirring bar was dissolved acetophenone derivative (15 mmol, 1 equiv) in methanol (100 mL) and 50% w/v KOH (17 mL). The reaction was stirred at 0° C. for 30 min. The aldehyde (18 mmol, 1.2 equiv) was added in one portion, and the mixture was stirred at 23° C. for 12-24 h. The solution was neutralized with 12 M HCl. The precipitate was removed by vacuum filtration, washed with water, dried, and recrystallized from methanol or dichloromethane/hexanes. When no precipitate was formed upon neutralization, the solution was extracted with EtOAc, and the combined organics were dried over sodium sulfate and concentrated under reduced pressure. The residue was purified by flash chromatography using 10% EtOAc/hexanes or recrystallization with hot methanol to afford the chalcones as a yellow solid.

Example 2

General Procedure for the Synthesis of Bis-Acetates

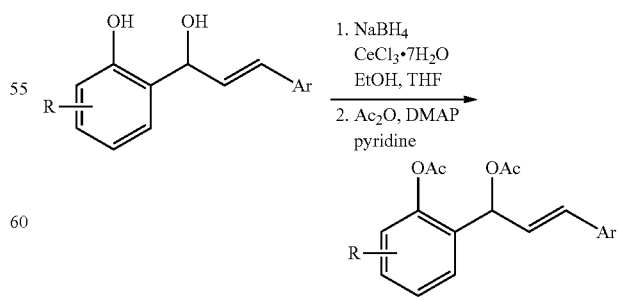

Into a round bottom flask equipped with magnetic stir bar was loaded 2'-hydroxychalcone derivative (2.5 mmol, 1 equiv), CeCl$_3$.7H$_2$O (5.5 mmol, 2.2 equiv), ethanol (200 proof, 8.8 equiv), and THF (0.1 M 25 mL). The mixture was cooled to 0° C. before NaBH$_4$ (5.5 mmol, 2.2 equiv) was added in one portion and allowed to slowly warmed to 23° C. Upon consumption of the 2'-hydroxychalcone, 4-dimethylaminopyridine (3.75 mmol, 1.5 equiv), pyridine (37.5 mmol, 15 equiv), and acetic anhydride (37.5 mmol, 15 equiv) were successively added. The reaction was stirred for 12-18 h and concentrated. The unpurified residue was taken up in EtOAc and quenched with a saturated solution of sodium bicarbonate. The layers were separated and the aqueous layer was back extracted with EtOAc. The combined organics were washed with DI H$_2$O, saturated copper (II) sulfate, and brine, dried over sodium sulfate, filtered, and concentrated under reduced pressure. The residue was purified by flash chromatography using EtOAc/hexanes to afford the corresponding bis-acetates.

Example 3

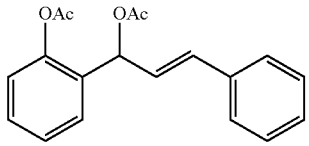 [SMILES: CC(=O)Oc1ccccc1C(/C=C/c1ccccc1)OC(C)=O]

(E)-1-(2-Acetoxy-3-methylphenyl)-3-phenylallyl acetate (1a)

Prepared according to the general procedure using (E)-2-(1-hydroxy-3-phenylallyl)-phenol. The residue was purified by flash chromatography using 15% EtOAc/hexanes to afford 1a as a clear crystal (450 mg, 74%). Analytical data for 1a: $^1$H NMR (500 MHz, CDCl$_3$) δ 7.52 (dt, J=7.7, 1.5 Hz, 1H), 7.39-7.34 (m, 3H), 7.35-7.23 (m, 4H), 7.11 (dt, J=8.1, 1.3 Hz, 1H), 6.62 (d, J=16.0, 1H), 6.61 (d, J=6.5 Hz, 1H), 6.35 (dd, J=15.8, 6.6 Hz, 1H), 2.32 (s, 3H), 2.11 (s, 3H); $^{13}$C NMR (125 MHz, CDCl$_3$) δ 170.0, 169.5, 148.4, 136.2, 132.9, 131.1, 129.5, 128.7, 128.6, 128.3, 126.8, 126.5, 126.2, 123.3, 71.3, 21.3, 21.2; IR (film): 3061, 3027, 2938, 1765, 1738, 1650, 1586, 1491, 1452, 1369, 1233, 1197, 1173, 1098, 1063, 1015, 964, 911, 877 cm$^{-1}$; LRMS (ESI): Mass calculated for [M+H]$^+$ C$_{19}$H$_{19}$O$_4$: 311.1; found: 311.1.

Example 4

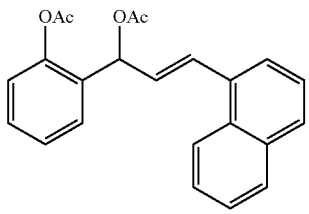 [SMILES: CC(=O)Oc1ccccc1C(/C=C/c1cccc2ccccc12)OC(C)=O]

(E)-2-(1-Acetoxy-3-(naphthalen-1-yl)allyl)phenyl acetate (1b)

Prepared according to the general procedure using (E)-1-(2-hydroxyphenyl)-3-(naphthalen-1-yl)prop-2-en-1-one. The residue was purified by flash chromatography using 15% EtOAc/hexanes to afford 1b as a colorless oil (290 mg, 40%). Analytical data for 1b: $^1$H NMR (500 MHz, CDCl$_3$) δ 8.05 (d, J=8.6, 1H), 7.85 (d, J=8.0 Hz, 1H), 7.79 (d, J=8.1 Hz, 1H), 7.59 (dd, J=7.8, 1.7 Hz, 1H), 7.57 (d, J=7.2 Hz, 1H), 7.55-7.47 (m, 2H), 7.49-7.39 (m, 3H), 7.34 (td, J=7.6, 1.3 Hz, 1H), 7.17 (dd, J=8.0, 1.3 Hz, 1H), 6.76 (dd, J=6.5, 1.3 Hz, 1H), 6.41 (dd, J=15.6, 6.5 Hz, 1H), 2.36 (s, 3H), 2.18 (s, 3H); $^{13}$C NMR (125 MHz, CDCl$_3$) δ 170.0, 169.6, 148.5, 134.0, 133.7, 131.3, 131.1, 130.4, 129.6, 129.4, 128.8, 128.7, 128.6, 126.5, 126.4, 126.0, 125.7, 124.3, 123.8, 123.4, 71.5, 21.4, 21.2; IR (film): 3060, 3046, 3014, 2936, 1765, 1737, 1369, 1233, 1198 cm$^{-1}$; LRMS (ESI): Mass calculated for [M+H]$^+$ C$_{23}$H$_{21}$O$_4$: 361.1; found: 361.0.

Example 5

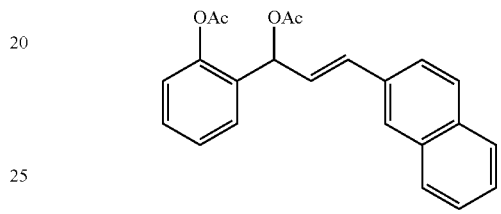

(E)-2-(1-Acetoxy-3-(naphthalen-2-yl)allyl)phenyl acetate (1c)

Prepared according to the general procedure using (E)-1-(2-hydroxyphenyl)-3-(naphthalen-2-yl)prop-2-en-1-one. The residue was purified by flash chromatography using 15% EtOAc/hexanes to afford 1c as a colorless oil (250 mg, 57%). Analytical data for 1c: $^1$H NMR (500 MHz, CDCl$_3$) δ 7.81-7.73 (m, 4H), 7.57 (ddd, J=9.4, 8.2, 1.7 Hz, 2H), 7.49-7.42 (m, 2H), 7.38 (td, J=7.6, 1.7 Hz, 1H), 7.30 (td, J=7.6, 1.3 Hz, 1H), 7.12 (dd, J=8.1, 1.2 Hz, 1H), 6.78 (d, J=15.9 Hz, 1H), 6.67 (dd, J=6.5, 1.3 Hz, 1H), 6.47 (dd, J=15.9, 6.4 Hz, 1H), 2.33 (s, 3H), 2.14 (s, 3H); $^{13}$C NMR (125 MHz, CDCl$_3$) δ 170.0, 169.6, 148.4, 133.63, 133.59, 133.3, 133.0, 131.1, 129.5, 128.8, 128.4, 128.2, 127.8, 127.2, 126.54, 126.51, 126.49, 126.3, 123.6, 123.3, 71.3, 21.3, 21.2; IR (film): 3057, 2936, 2854, 1766, 1737, 1651, 1607, 1507, 1369, 1233, 1198, 1174 cm$^{-1}$; LRMS (ESI): Mass calculated for [M+H]$^+$ C$_{23}$H$_{21}$O$_4$: 361.1; found: 361.3.

Example 6

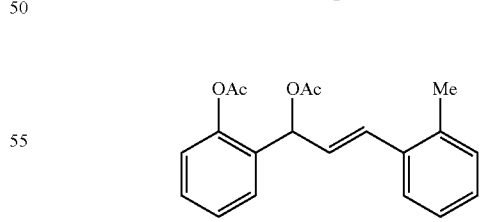

(E)-2-(1-Acetoxy-3-(o-tolyl)allyl)phenyl acetate (1d)

Prepared according to the general procedure using (E)-1-(2-hydroxyphenyl)-3-(o-tolyl)prop-2-en-1-one. The residue was purified by flash chromatography using 15% EtOAc/hexanes to afford 1d as a colorless oil (290 mg, 40%).

Analytical data for 1d: $^1$H NMR (500 MHz, CDCl$_3$) δ 7.53 (dd, J=7.7, 1.6 Hz, 1H), 7.46-7.40 (m, 1H), 7.37 (td, J=7.8, 1.7 Hz, 1H), 7.28 (td, J=7.6, 1.2 Hz, 1H), 7.19-7.09 (m, 4H), 6.85 (dd, J=15.9, 1.3 Hz, 1H), 6.62 (dd, J=6.6, 1.3 Hz, 1H), 6.24 (dd, J=15.7, 6.6 Hz, 1H), 2.34 (s, 3H), 2.33 (s, 3H), 2.11 (s, 3H). $^{13}$C NMR (125 MHz, CDCl$_3$) δ 169.9, 169.4, 148.3, 135.8, 135.2, 131.1, 130.9, 130.4, 129.4, 128.6, 128.0, 127.4, 126.4, 126.2, 125.8, 123.2, 71.5, 21.2, 21.1, 19.8; IR (film): 3098, 3063, 3017, 2912, 2860, 1924, 1724, 1719, 1572, 1463, 1426 cm$^{-1}$; LRMS (ESI): Mass calculated for [M+H]$^+$ C$_{20}$H$_{21}$O$_4$: 325.1; found: 325.5.

Example 7

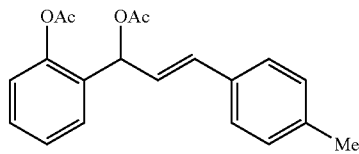 [SMILES: CC(=O)Oc1ccccc1C(/C=C/c1ccc(C)cc1)OC(C)=O]

(E)-2-(1-Acetoxy-3-(p-tolyl)allyl)phenyl acetate (1e)

Prepared according to the general procedure using (E)-1-(2-hydroxyphenyl)-3-(p-tolyl)prop-2-en-1-one. The residue was purified by flash chromatography using 15% EtOAc/hexanes to afford 1e as a colorless oil (170 mg, 62%). Analytical data for 1e: $^1$H NMR (500 MHz, CDCl$_3$) δ 7.52 (dd, J=7.7, 1.7 Hz, 1H), 7.36 (td, J=7.7, 1.7 Hz, 1H), 7.29-7.26 (m, 3H), 7.11 (d, J=8.1 Hz, 2H), 7.10 (dd, J=8.3, 1.3 Hz, 1H), 6.60 (d, J=7.5 Hz, 1H), 6.59 (d, J=15.4 Hz, 1H), 6.34-6.25 (m, 1H), 2.33 (s, 3H), 2.31 (s, 3H), 2.11 (s, 3H); $^{13}$C NMR (125 MHz, CDCl$_3$) δ 170.0, 169.5, 148.4, 138.2, 133.4, 132.9, 131.2, 129.4, 128.7, 126.7, 126.4, 125.1, 123.3, 71.4, 21.4, 21.3, 21.2; IR (film): 3087, 3023, 2973, 2921, 2858, 1777, 1769, 1588, 1371, 1282, 1245 cm$^{-1}$; LRMS (ESI): Mass calculated for [M+H]$^+$ C$_{20}$H$_{21}$O$_4$: 325.1.

Example 8

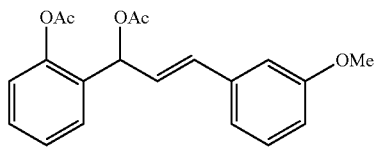 [SMILES: COc1cccc(/C=C/C(OC(C)=O)c2ccccc2OC(C)=O)c1]

(E)-2-(1-Acetoxy-3-(3-methoxyphenyl)allyl)phenyl acetate (1f)

Prepared according to the general procedure using (E)-1-(2-hydroxyphenyl)-3-(3-methoxyphenyl)prop-2-en-1-one. The residue was purified by flash chromatography using 15% EtOAc/hexanes to afford 1f as a colorless oil (330 mg, 42%). Analytical data for 1f: $^1$H NMR (500 MHz, CDCl$_3$) δ 7.52 (dd, J=7.7, 1.7 Hz, 1H), 7.37 (ddd, J=8.1, 7.4, 1.7 Hz, 1H), 7.28 (td, J=8.1, 1.5 Hz, 1H), 7.23 (t, J=7.9 Hz, 1H), 7.11 (dd, J=8.1, 1.2 Hz, 1H), 6.97 (dt, J=7.6, 1.2 Hz, 1H), 6.90 (dd, J=2.6, 1.5 Hz, 1H), 6.81 (ddd, J=8.3, 2.6, 0.9 Hz, 1H), 6.61 (d, J=6.5 Hz, 1H), 6.60 (d, J=15.9 Hz, 1H), 6.34 (dd, J=15.6, 6.7 Hz, 1H), 3.80 (s, 3H), 2.32 (s, 3H), 2.11 (s, 3H); $^{13}$C NMR (125 MHz, CDCl$_3$) δ 169.7, 169.3, 159.6, 148.1, 137.3, 132.5, 130.8, 129.5, 129.2, 128.5, 126.25, 126.20, 123.0, 119.2, 113.7, 111.7, 70.9, 55.1, 21.0, 20.9; IR (film): 3063, 3038, 3005, 2959, 2940, 1766, 1599, 1489, 1466, 1370, 1234, 1042 cm$^{-1}$; LRMS (ESI): Mass calculated for [M+H]$^+$ C$_{20}$H$_{21}$O$_5$: 341.1; found 341.1.

Example 9

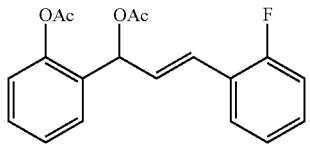 [SMILES: CC(=O)Oc1ccccc1C(/C=C/c1ccccc1F)OC(C)=O]

(E)-2-(1-Acetoxy-3-(2-fluorophenyl)allyl)phenyl acetate (1g)

Prepared according to the general procedure using (E)-3-(2-fluorophenyl)-1-(2-hydroxyphenyl)prop-2-en-1-one. The residue was purified by flash chromatography using 15% EtOAc/hexanes to afford 1g as a colorless oil (229 mg, 47%). Analytical data for 1g: $^1$H NMR (500 MHz, CDCl$_3$) δ 7.52 (dd, J=7.7, 1.7 Hz, 1H), 7.42 (td, J=7.7, 1.7 Hz, 1H), 7.37 (td, J=7.7, 1.7 Hz, 1H), 7.28 (dd, J=7.6, 1.3 Hz, 1H), 7.22 (dddd, J=8.1, 7.1, 5.2, 1.8 Hz, 1H), 7.11 (dd, J=8.2, 1.3 Hz, 1H), 7.08 (td, J=7.6, 1.2 Hz, 1H), 7.03 (ddd, J=10.8, 8.3, 1.2 Hz, 1H), 6.80 (dd, J=16.3, 1.2 Hz, 1H), 6.61 (dd, J=6.6, 1.3 Hz, 1H), 6.43 (dd, J=16.1, 6.5 Hz, 1H), 2.33 (s, 3H), 2.12 (s, 3H); $^{13}$C NMR (125 MHz, CDCl$_3$) δ 169.9, 169.5, 160.5 (d, J=249.8 Hz), 148.4, 130.9, 129.56 (d, J=8.6 Hz), 129.56, 128.74 (d, J=5.5 Hz), 128.69, 127.8 (d, J=3.5 Hz), 126.5, 125.1 (d, J=3.6 Hz), 124.3 (d, J=3.6 Hz), 124.0 (d, J=12.0 Hz), 123.3, 115.9 (d, J=22.0 Hz), 71.3, 21.3, 21.2; $^{19}$F NMR (376 MHz, CDCl$_3$) δ −117.57; IR (film): 3064, 3040, 2935, 2853, 1766, 1741, 1609, 1579, 1488, 1455, 1370, 1231, 1199, 1174, 1096, 1066, 1016, 968 cm$^{-1}$; LRMS (ESI): Mass calculated for [M+H]$^+$ C$_{19}$H$_{18}$FO$_4$: 329.1; found: 329.2.

Example 10

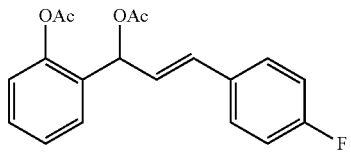 [SMILES: CC(=O)Oc1ccccc1C(/C=C/c1ccc(F)cc1)OC(C)=O]

(E)-2-(1-Acetoxy-3-(4-fluorophenyl)allyl)phenyl acetate (1h)

Prepared according to the general procedure using (E)-3-(4-fluorophenyl)-1-(2-hydroxyphenyl)prop-2-en-1-one. The residue was purified by flash chromatography using 15% EtOAc/hexanes to afford 1h as a white solid (285 mg, 39%). Analytical data for 1h: $^1$H NMR (500 MHz, CDCl$_3$) δ 7.51 (dd, J=7.7, 1.7 Hz, 1H), 7.40-7.30 (m, 3H), 7.29 (dd, J=7.6, 1.3 Hz, 1H), 7.10 (dd, J=8.1, 1.3 Hz, 1H), 6.99 (t, J=8.7 Hz, 2H), 6.59-6.55 (m, 2H) 6.26 (dd, J=15.6, 6.9 Hz, 1H), 2.31 (s, 3H), 2.11 (s, 3H); $^{13}$C NMR (125 MHz, CDCl$_3$) δ 170.0, 169.5, 162.7 (d, J=247.8 Hz), 148.3, 132.3 (d, J=3.2 Hz), 131.8, 131.0, 129.5, 128.7, 128.4 (d, J=8.0 Hz), 126.5, 126.0 (d, J=2.3 Hz), 123.3, 115.7 (d, J=21.7 Hz), 71.2, 21.3, 21.2; $^{19}$F NMR (376 MHz, CDCl$_3$) δ −113.62; IR (film): 3041, 2937, 1769, 1765, 1736, 1729, 1655, 1601, 1509, 1489, 1453, 1431, 1371, 1297, 1158, 1096, 1040, 1012, 970 cm$^{-1}$; LRMS (ESI): Mass calculated for [M−H]$^-$ C$_{19}$H$_{16}$FO$_4$: 327.1; found: 327.0.

Example 11

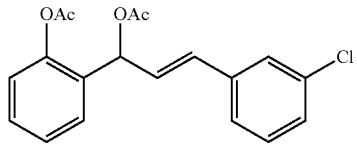 [SMILES: CC(=O)Oc1ccccc1C(/C=C/c1cccc(Cl)c1)OC(C)=O]

(E)-2-(1-Acetoxy-3-(3-chlorophenyl)allyl)phenyl acetate (1i)

Prepared according to the general procedure using (E)-3-(3-chlorophenyl)-1-(2-hydroxyphenyl)prop-2-en-1-one.
The residue was purified by flash chromatography using 15% EtOAc/hexanes to afford 1i as a colorless oil (683 mg, 64%). Analytical data for 1i: $^1$H NMR (500 MHz, CDCl$_3$) δ 7.53 (dd, J=7.7, 1.6 Hz, 1H), 7.41 (dd, J=7.7, 1.7 Hz, 1H), 7.39 (t, J=1.6 Hz, 1H), 7.31 (td, J=7.6, 1.2 Hz, 1H), 7.26 (m, 3H), 7.14 (dd, J=8.1, 1.3 Hz, 1H), 6.63 (dd, J=6.2, 1.3 Hz, 1H), 6.58 (dd, J=15.9, 1.4 Hz, 1H), 6.39 (dd, J=15.9, 6.3 Hz, 1H), 2.35 (s, 3H), 2.14 (s, 3H); $^{13}$C NMR (125 MHz, CDCl$_3$) δ 169.9, 169.5, 148.4, 138.0, 134.7, 131.3, 130.8, 130.0, 129.6, 128.7, 128.2, 127.8, 126.7, 126.5, 125.1, 123.3, 70.9, 21.25, 21.18; IR (film): 3064, 3038, 2936, 2850, 1765, 1739, 1593, 1566, 1489, 1453, 1428, 1369, 1232, 1198, 1174, 1096, 1077, 1066, 1015, 962, 911, 777, 757 cm$^{-1}$; LRMS (ESI): Mass calculated for [M+H]$^+$ C$_{19}$H$_{18}$ClO$_4$: 345.1; found: 345.1.

Example 12

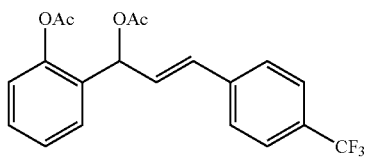 [SMILES: CC(=O)Oc1ccccc1C(/C=C/c1ccc(C(F)(F)F)cc1)OC(C)=O]

(E)-2-(1-Acetoxy-3-(4-(trifluoromethyl)phenyl)allyl) phenyl acetate (1j)

Prepared according to the general procedure using (E)-1-(2-hydroxyphenyl)-3-(4-(trifluoromethyl)phenyl)prop-2-en-1-one. The residue was purified by flash chromatography using 15% EtOAc/hexanes to afford 1j as a colorless oil (230 mg, 49%). Analytical data for 1j: $^1$H NMR (500 MHz, CDCl$_3$) δ 7.56 (d, J=8.1 Hz, 2H), 7.50 (dd, J=7.7, 1.7 Hz, 1H), 7.46 (d, J=8.2 Hz, 2H), 7.38 (td, J=7.8, 1.7 Hz, 1H), 7.29 (td, J=7.5, 1.3 Hz, 1H), 7.11 (dd, J=8.0, 1.2 Hz, 1H), 6.63 (d, J=15.9 Hz, 1H), 6.62 (d, J=6.5 Hz, 1H) 6.43 (dd, J=15.9, 6.2 Hz, 1H), 2.32 (s, 3H), 2.13 (s, 3H); $^{13}$C NMR (125 MHz, CDCl$_3$) δ 169.9, 169.5, 148.4, 139.7, 131.2, 130.7, 130.0 (d, J=32.4 Hz), 129.7, 129.0, 128.8, 127.0, 126.6, 125.7 (q, J=3.8 Hz), 124.2 (d, J=272.0 Hz), 123.4, 70.8, 21.3, 21.2; $^{19}$F NMR (376 MHz, CDCl$_3$) δ −62.62; IR (film): 3085, 3044, 2937, 1926, 1782, 1726, 1657, 1615, 1587, 1494, 1455, 1415, 1365, 1316, 1282, 1252, 1137, 1097 cm$^{-1}$; LRMS (ESI): Mass calculated for [M+H]$^+$ C$_{20}$H$_{18}$F$_3$O$_4$: 379.1; found: 379.2.

Example 13

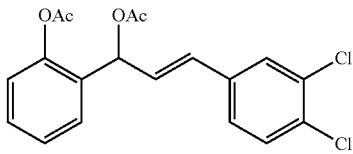 [SMILES: CC(=O)Oc1ccccc1C(/C=C/c1ccc(Cl)c(Cl)c1)OC(C)=O]

(E)-2-(1-Acetoxy-3-(3,4-dichlorophenyl)allyl)phenyl acetate (1k)

Prepared according to the general procedure using its (E)-3-(3,4-dichlorophenyl)-1-(2-hydroxyphenyl)prop-2-en-1-one. The residue was purified by flash chromatography using 15% EtOAc/hexanes to afford 1k as a colorless oil (230 mg, 28%). Analytical data for 1k: $^1$H NMR (500 MHz, CDCl$_3$) δ 7.39 (dd, J=7.7, 1.7 Hz, 1H), 7.35 (s, 1H), 7.31-7.26 (m, 2H), 7.22-7.14 (m, 1H), 7.08 (dd, J=8.3, 2.1 Hz, 1H), 7.01 (dd, J=8.0, 1.3 Hz, 1H), 6.49 (dd, J=6.1, 1.4 Hz, 1H), 6.40 (dd, J=15.9, 1.4 Hz, 1H), 6.24 (dd, J=15.9, 6.2 Hz, 1H), 2.22 (s, 3H), 2.02 (s, 3H); $^{13}$C NMR (125 MHz, CDCl$_3$) δ 169.9, 169.5, 148.3, 136.3, 132.9, 131.9, 130.64, 130.60, 130.2, 129.7, 128.7, 128.5, 128.4, 126.6, 126.0, 123.3, 70.7, 21.24, 21.18; IR (film): 3063, 3038, 2926, 2852, 1767, 1739, 1608, 1587, 1554, 1473, 1454, 1431, 1370, 1233, 1198, 1174, 1133, 1026 cm$^{-1}$; LRMS (ESI): Mass calculated for [M+H]$^+$ C$_{19}$H$_{17}$C$_{12}$O$_4$: 379.1; found: 379.1.

Example 14

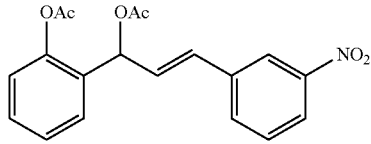 [SMILES: CC(=O)Oc1ccccc1C(/C=C/c1cccc([N+](=O)[O-])c1)OC(C)=O]

(E)-2-(1-Acetoxy-3-(3-nitrophenyl)allyl)phenyl acetate (1l)

Prepared according to the general procedure using (E)-1-(2-hydroxyphenyl)-3-(3-nitrophenyl)prop-2-en-1-one. The residue was purified by flash chromatography using 15% EtOAc/hexanes to afford 1l as a colorless oil (352 mg, 54%). Analytical data for 1l: $^1$H NMR (500 MHz, CDCl$_3$) δ 8.23 (t, J=1.9 Hz, 1H), 8.10 (ddd, J=8.4, 2.3, 1.1 Hz, 1H), 7.66 (dt, J=8.0, 1.3 Hz, 1H), 7.57-7.45 (m, 2H), 7.40 (td, J=7.8, 1.7 Hz, 1H), 7.30 (td, J=7.6, 1.3 Hz, 1H), 7.12 (dd, J=8.1, 1.3 Hz, 1H), 6.65 (d, J=16.0 Hz, 1H), 6.63 (d, J=6.0 Hz, 1H), 6.49 (dd, J=16.0, 5.9 Hz, 1H), 2.34 (s, 3H), 2.20 (s, 3H); $^{13}$C NMR (125 MHz, CDCl$_3$) δ 169.9, 169.5, 148.7, 148.4, 138.0, 132.6, 130.4, 130.2, 129.8, 129.7 (2C), 128.8, 126.6, 123.4, 122.8, 121.4, 70.6, 21.24, 21.20; IR (film): 3087, 3068, 3039, 2937, 2869, 2310, 2281, 1825, 1780, 1721, 1656, 1608, 1587, 1490, 1431, 1378, 1341, 1262, 1158, 1043, 1023, 975 cm$^{-1}$; LRMS (ESI): Mass calculated for [M+H]$^+$ C$_{19}$H$_{18}$NO$_6$: 356.1; found: 356.2.

Example 15

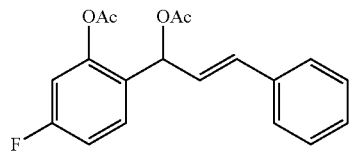 [SMILES: CC(=O)Oc1cc(F)ccc1C(/C=C/c1ccccc1)OC(C)=O]

(E)-2-(1-Acetoxy-3-phenylallyl)-5-fluorophenyl acetate (1m)

Prepared according to the general procedure using (E)-1-(4-fluoro-2-hydroxyphenyl)-3-phenylprop-2-en-1-one. The residue was purified by flash chromatography using 15% EtOAc/hexanes to afford 1m as a colorless oil (485 mg, 70%). Analytical data for 1m: $^1$H NMR (500 MHz, CDCl$_3$) δ 7.48 (dd, J=8.7, 6.2 Hz, 1H), 7.39-7.27 (m, 5H), 6.99 (ddd, J=8.6, 7.9, 2.6 Hz, 1H), 6.89 (dd, J=9.1, 2.6 Hz, 1H), 6.60 (d, J=16.0 Hz, 1H), 6.57 (dd, J=6.4, 1.4 Hz, 1H), 6.32 (dd, J=15.9, 6.4 Hz, 1H), 2.32 (s, 3H), 2.10 (s, 3H); $^{13}$C NMR (125 MHz, CDCl$_3$) δ 169.9, 169.0, 162.5 (d, J=249.3 Hz), 149.1 (d, J=10.9 Hz), 136.0, 132.9, 129.9 (d, J=9.6 Hz), 128.8, 128.4, 127.2 (d, J=3.6 Hz), 126.8, 126.0, 113.6 (d, J=21.3 Hz), 111.2 (d, J=24.4 Hz), 70.7, 21.3, 21.1; $^{19}$F NMR (376 MHz, CDCl$_3$) δ -112.10; IR (film): 3082, 3028, 2938, 1951, 1890, 1732, 1651, 1603, 1578, 1504, 1425, 1371, 1235, 1143, 1091 and 1015 cm$^{-1}$; LRMS (ESI): Mass calculated for [M+H]$^+$ C$_{19}$H$_{18}$FO$_4$: 329.1; found: 329.2.

Example 16

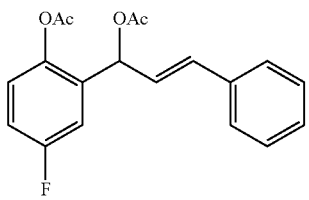 [SMILES: CC(=O)Oc1ccc(F)cc1C(/C=C/c1ccccc1)OC(C)=O]

(E)-2-(1-Acetoxy-3-phenylallyl)-4-fluorophenyl acetate (1n)

Prepared according to the general procedure using (E)-1-(5-fluoro-2-hydroxyphenyl)-3-phenylprop-2-en-1-one. The residue was purified by flash chromatography using 15% EtOAc/hexanes to afford 1n as a yellow oil (382.1 mg, 63%). Analytical data for 1n: $^1$H NMR (500 MHz, CDCl$_3$) δ 7.39-7.29 (m, 4H), 7.28-7.24 (m, 1H), 7.22 (dd, J=8.9, 2.8 Hz, 1H), 7.10-7.02 (m, 2H), 6.63 (dd, J=15.9, 1.3 Hz, 1H), 6.56 (dd, J=6.8, 1.3 Hz, 1H), 6.28 (dd, J=15.9, 6.6 Hz, 1H), 2.30 (s, 3H), 2.13 (s, 3H); $^{13}$C NMR (125 MHz, CDCl$_3$) δ 169.8, 169.5, 160.4 (d, J=245.3 Hz), 144.0 (d, J=2.9 Hz), 135.9, 133.5, 133.1 (d, J=7.4 Hz), 128.8, 128.4, 126.8, 125.5, 124.7 (d, J=8.5 Hz), 116.1 (d, J=23.4 Hz), 115.1 (d, J=24.4 Hz), 70.7, 21.3, 21.1; $^{19}$F NMR (376 MHz, CDCl$_3$) δ -115.63; IR (film): 3082, 3060, 3028., 2935, 2851, 1766, 1651, 1619, 1579, 1494, 1370, 1269, 1205, 1171, 1065, 1017, 968, 941, 901, 879 cm$^{-1}$; LRMS (ESI): Mass calculated for [M+H]$^+$ C$_{19}$H$_{18}$FO$_4$: 329.1; found: 329.1.

Example 17

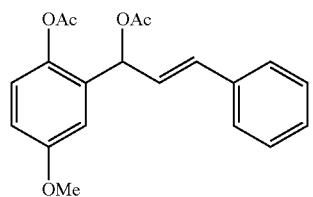 [SMILES: COc1ccc(OC(C)=O)c(C(/C=C/c2ccccc2)OC(C)=O)c1]

(E)-2-(1-Acetoxy-3-phenylallyl)-4-methoxyphenyl acetate (1o)

Prepared according to the general procedure using (E)-1-(2-hydroxy-5-methoxyphenyl)-3-phenylprop-2-en-1-one. The residue was purified by flash chromatography using 15% EtOAc/hexanes to afford 1o as a colorless oil (380 mg, 61%). Analytical data for 1o: $^1$H NMR (500 MHz, CDCl$_3$) δ 7.37 (d, J=7.0 Hz, 2H), 7.31 (t, J=7.4 Hz, 2H), 7.24 (d, J=7.3 Hz, 1H), 7.03 (d, J=1.8 Hz, 1H), 7.02 (d, J=4.1 Hz, 1H), 6.88 (dd, J=8.9, 3.1 Hz, 1H), 6.62 (dd, J=15.9, 1.3 Hz, 1H), 6.55 (dd, J=6.5, 1.4 Hz, 1H), 6.32 (dd, J=15.9, 6.5 Hz, 1H), 3.81 (s, 3H), 2.29 (s, 3H), 2.12 (s, 3H); $^{13}$C NMR (125 MHz, CDCl$_3$) δ 169.93, 169.91, 157.6, 141.7, 136.1, 133.0, 132.0, 128.7, 128.3, 126.8, 126.0, 124.0, 114.2, 113.9, 71.2, 55.8, 21.3, 21.1; IR (film): 3086, 3061, 3032, 2999, 2917, 2849, 2832, 1608, 1578, 1488, 1433, 1372, 1307, 1269, 1165, 1029 cm$^{-1}$; LRMS (ESI): Mass calculated for [M+H]$^+$ C$_{20}$H$_{21}$O$_5$: 341.1; found 341.1.

Example 18

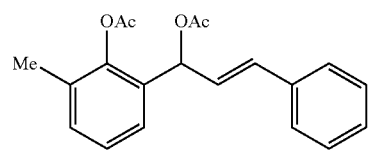 [SMILES: CC(=O)Oc1c(C)cccc1C(/C=C/c1ccccc1)OC(C)=O]

(E)-1-(2-Acetoxy-3-methylphenyl)-3-phenylallyl acetate (1p)

Prepared according to the general procedure using (E)-1-(2-hydroxy-3-methylphenyl)-3-phenylprop-2-en-1-one. The residue was purified by flash chromatography using 15% EtOAc/hexanes to afford 1p as a yellow oil (280 mg, 47%). Analytical data for 1p: $^1$H NMR (500 MHz, CDCl$_3$) δ 7.40-7.15 (m, 8H), 6.62 (dd, J=15.9, 1.4 Hz, 1H), 6.55 (m, 1H), 6.36 (dd, J=15.9, 6.5 Hz, 1H), 2.33 (s, 3H), 2.17 (s, 3H), 2.10 (s, 3H); $^{13}$C NMR (125 MHz, CDCl$_3$) δ 170.0, 169.0, 147.4, 136.2, 131.5, 131.4, 131.3, 128.7, 128.2, 127.3, 126.8, 126.5, 126.4, 126.3, 76.2, 21.3, 20.9, 16.5; IR (film): 3060, 3027, 2957, 2925, 2855, 1762, 1740, 1598, 1577, 1496, 1468, 1437, 1369, 1232, 1209, 1165, 1089, 1016, 966 and 907 cm$^{-1}$; LRMS (ESI): Mass calculated for [M+H]$^+$ C$_{20}$H$_{21}$O$_4$: 325.1; found: 325.1.

Example 19

General Procedure for Enantioselective Synthesis of Chromenes

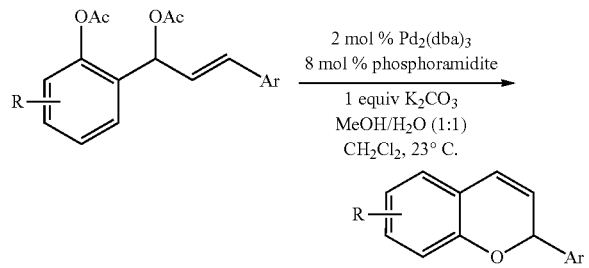

Into an oven-dried, screw-capped reaction tube-vial equipped with magnetic stirbar was loaded bis-acetate (0.36 mmol, 1 equiv). The vial was taken into a nitrogen-filled drybox at which time Pd$_2$(dba)$_3$ (7.2 μmol, 0.02 equiv) and phosphoramidite (29 μmol, 0.08 equiv) were added. The vial was capped with a septum cap, removed from the drybox and put under positive N$_2$ pressure. The mixture was diluted with CH$_2$Cl$_2$ (3.6 mL) and stirred for 10 min under static nitrogen pressure. A solution of K$_2$CO$_3$ (0.36 mmol, 1 equiv) in methanol:water (1.8 mL:1.8 mL) was added. The resulting biphasic mixture was stirred at 23° C. for 19-48 h. Reaction was extracted with CH$_2$Cl$_2$. The combined organic layers were filtered through a Biotage ISOLUTE® phase separator, and the organic filtrate was concentrated under reduced pressure. The residue was purified by flash chromatography using EtOAc/hexanes to afford the corresponding chromene.

Example 20

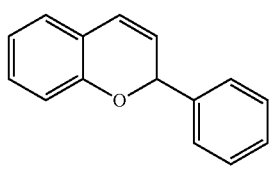 [SMILES: C1=CC(c2ccccc2)Oc2ccccc21]

2-Phenyl-2H-chromene (2a)

Prepared according to the general procedure using 1a. The residue was purified by flash chromatography using 1% EtOAc/hexanes to afford 2a as a light yellow oil (53 mg, 71%). Analytical data for 2a: $^1$H NMR (500 MHz, CDCl$_3$) δ 7.52-7.43 (m, 2H), 7.43-7.36 (m, 2H), 7.36-7.31 (m, 1H), 7.12 (td, J=7.8, 1.7 Hz, 1H), 7.02 (dd, J=7.5, 1.7 Hz, 1H), 6.87 (td, J=7.4, 1.1 Hz, 1H), 6.80 (d, J=8.1 Hz, 1H), 6.54 (dd, J=9.8, 1.9 Hz, 1H), 5.93 (dd, J=3.4, 1.9 Hz, 1H), 5.81 (dd, J=9.8, 3.4 Hz, 1H); $^{13}$C NMR (125 MHz, CDCl$_3$) δ 153.5, 141.2, 129.9, 129.1, 128.8, 127.4, 127.0, 125.2, 124.4, 121.7, 121.6, 116.4, 77.5; IR (film): 3043, 2919, 2851, 1573, 1510, 1485, 1456, 1227, 1201, 1112, 1060, 857 cm$^{-1}$; HRMS (EI): Mass calculated for [M]$^+$ C$_{15}$H$_{12}$O: 208.0888; found 208.0869; Enantiomeric ratio was measured by chiral phase HPLC (Chiralcel OJ-H; 100% hexanes; 0.7 mL/min, 280 nm), Rt$_1$ (minor)=61.4, Rt$_2$ (major)=74.8 min; er=95:5. The absolute configuration of the chromenes was determined by comparison of optical rotation to literature value of the known enantiomer.

Example 21

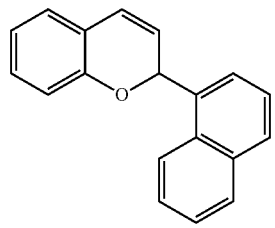 [SMILES: C1=CC(c2cccc3ccccc23)Oc2ccccc21]

2-(Naphthalen-1-yl)-2H-chromene (2b)

Prepared according to the general procedure using 1b. The residue was purified by flash chromatography using 1% EtOAc/hexanes to afford 2b as a light yellow oil (66 mg, 71%). Analytical data for 2b: $^1$H NMR (500 MHz, CDCl$_3$) δ 8.32 (d, J=8.4 Hz, 1H), 7.90 (dd, J=7.9, 1.7 Hz, 1H), 7.84 (d, J=8.2 Hz, 1H), 7.65 (dd, J=7.0, 1.1 Hz, 1H), 7.54 (dddd, J=20.2, 8.0, 6.7, 1.4 Hz, 2H), 7.45 (dd, J=8.2, 7.1 Hz, 1H), 7.11 (td, J=7.7, 1.7 Hz, 1H), 7.08 (dd, J=7.4, 1.6 Hz, 1H), 6.90 (td, J=7.4, 1.1 Hz, 1H), 6.79 (d, J=8.0 Hz, 1H), 6.65 (dd, J=9.7, 2.1 Hz, 1H), 6.62 (t, J=2.7 Hz, 1H), 5.92 (dd, J=9.8, 3.3 Hz, 1H); $^{13}$C NMR (125 MHz, CDCl$_3$) δ 153.9, 135.8, 134.5, 131.3, 129.9, 129.6, 129.2, 127.1, 126.8, 126.24, 126.16, 125.7, 125.3, 125.2, 124.4, 122.0, 121.7, 116.6, 75.2; IR (film): 3072, 3042, 1640, 1605, 1510, 1485, 1456, 1307, 1228, 1200, 1112, 1060, 1036, 1010, 959, 944 cm$^{-1}$; HRMS (EI): Mass calculated for [M]$^+$ C$_{19}$H$_{14}$O: 258.1045; found 258.1036; Enantiomeric ratio was measured by chiral phase HPLC (Chiralcel OJ-H; 100% hexanes; 0.7 mL/min, 280 nm), Rt$_1$ (minor)=61.2, Rt$_2$ (major)=83.9 min; er=94:6.

Example 22

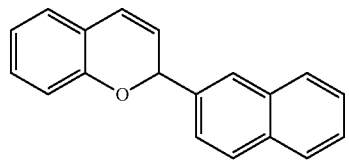 [SMILES: C1=CC(c2ccc3ccccc3c2)Oc2ccccc21]

2-(Naphthalen-2-yl)-2H-chromene (2c)

Prepared according to the general procedure using 1c. The residue was purified by flash chromatography using 1% EtOAc/hexanes to afford 2c as a light yellow oil (81 mg, 87%). Analytical data for 2c: $^1$H NMR (500 MHz, CDCl$_3$) δ 7.89-7.81 (m, 4H), 7.61 (dd, J=8.5, 1.8 Hz, 1H), 7.52-7.44

(m, 2H), 7.12 (td, J=7.8, 1.7 Hz, 1H), 7.04 (dd, J=7.5, 1.6 Hz, 1H), 6.88 (td, J=7.5, 1.2 Hz, 1H), 6.81 (dt, J=8.2, 1.0 Hz, 1H), 6.59 (ddd, J=10.0, 1.9, 0.8 Hz, 1H), 6.09 (dd, J=3.4, 1.9 Hz, 1H), 5.88 (dd, J=9.9, 3.4 Hz, 1H); $^{13}$C NMR (125 MHz, CDCl$_3$) δ 153.3, 138.2, 133.4, 133.3, 129.7, 128.8, 128.3, 127.8, 126.8, 126.4 (2C), 126.2, 125.1, 124.8, 124.4, 121.5, 121.4, 116.2, 77.4; IR (film): 3072, 1640, 1510, 1228 cm$^{-1}$; HRMS (EI): Mass calculated for [M]$^+$ C$_{19}$H$_{14}$O: 258.1045; found 258.1022; Enantiomeric ratio was measured by chiral phase HPLC (Whelk-O; 100% hexanes; 0.7 mL/min, 280 nm), Rt$_1$ (minor)=35.7, Rt$_2$ (major)=66.8 min; er=91:9.

Example 23

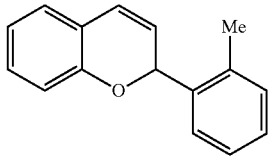 [SMILES: Cc1ccccc1C1C=Cc2ccccc2O1]

2-(o-Tolyl)-2H-chromene (2d)

Prepared according to the general procedure using 1d. The residue was purified by flash chromatography using 1% EtOAc/hexanes to afford 2d as a yellow oil (58 mg, 72%). Analytical data for 2d: $^1$H NMR (500 MHz, CDCl$_3$) δ 7.48 (dt, J=7.0, 1.2 Hz, 1H), 7.24-7.18 (m, 3H), 7.11 (td, J=7.8, 1.7 Hz, 1H), 7.02 (dd, J=7.4, 1.7 Hz, 1H), 6.87 (td, J=7.4, 1.1 Hz, 1H), 6.77 (dt, J=8.1, 0.9 Hz, 1H), 6.56 (dd, J=9.8, 2.1 Hz, 1H), 6.15 (dd, J=3.1, 2.1 Hz, 1H), 5.75 (dd, J=9.8, 3.2 Hz, 1H), 2.47 (s, 3H); $^{13}$C NMR (125 MHz, CDCl$_3$) δ 153.6, 138.4, 136.1, 131.0, 129.5, 128.5, 127.8, 126.7, 126.3, 124.7, 124.6, 121.5, 121.3, 116.1, 74.8, 19.4; IR (film): 3061, 3022, 2971, 2924, 1646, 1633, 1586, 1563, 1485 cm$^{-1}$; HRMS (EI): Mass calculated for [M]$^+$ C$_{16}$H$_{14}$O: 222.1045; found 222.1018; Enantiomeric ratio was measured by chiral phase HPLC (Whelk-O; 100% hexanes; 0.1 mL/min, 280 nm), Rt$_1$ (minor)=100.9, Rt$_2$ (major)=118.5 min; er=92:8.

Example 24

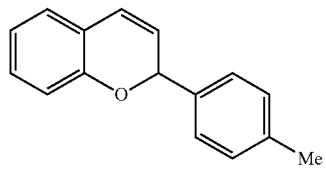 [SMILES: Cc1ccc(C2C=Cc3ccccc3O2)cc1]

2-(p-Tolyl)-2H-chromene (2e)

Prepared according to the general procedure using 1e. The residue was purified by flash chromatography using 1% EtOAc/hexanes to afford 2e as a yellow oil (58 mg, 73%). Analytical data for 2e: $^1$H NMR (500 MHz, CDCl$_3$) δ 7.39-7.35 (m, 2H), 7.20 (d, J=7.9 Hz, 2H), 7.12 (td, J=7.7, 1.7 Hz, 1H), 7.03 (dd, J=7.4, 1.7 Hz, 1H), 6.88 (td, J=7.5, 1.2 Hz, 1H), 6.80 (dt, J=8.1, 0.9 Hz, 1H), 6.55 (dd, J=9.9, 1.9 Hz, 1H), 5.90 (dd, J=3.4, 1.9 Hz, 1H), 5.81 (dd, J=9.8, 3.4 Hz, 1H), 2.37 (s, 3H); $^{13}$C NMR (125 MHz, CDCl$_3$) δ 153.3, 138.4, 138.0, 129.6, 129.5, 127.2, 126.7, 125.1, 124.1, 121.5, 121.3, 116.2, 77.4, 21.6; IR (film): 3044, 2958, 2851, 1633, 1484 cm$^{-1}$; HRMS (EI): Mass calculated for [M]$^+$ C$_{16}$H$_{14}$O: 222.1045; found 222.1015; Enantiomeric ratio was measured by chiral phase HPLC (Chiralcel OJ-H; 100% hexanes; 0.7 mL/min, 280 nm), Rt$_1$ (major)=62.3, Rt$_2$ (minor)=124.4 min; er=93:7.

Example 25

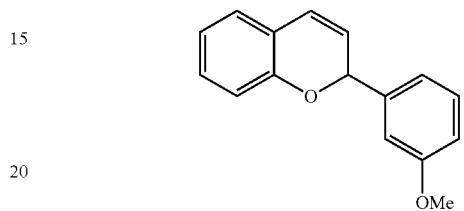

2-(3-Methoxyphenyl)-2H-chromene (2f)

Prepared according to the general procedure using 1f. The residue was purified by flash chromatography using 1.5% EtOAc/hexanes to afford 2f as a light yellow oil (67 mg, 78%). Analytical data for 2f: $^1$H NMR (500 MHz, CDCl$_3$) δ 7.29 (t, J=7.9 Hz, 1H), 7.14-7.08 (m, 1H), 7.06-6.98 (m, 3H), 6.89-6.84 (m, 2H), 6.80 (dt, J=8.0, 0.9 Hz, 1H), 6.55-6.50 (m, 1H), 5.91-5.87 (m, 1H), 5.79 (dd, J=9.8, 3.4 Hz, 1H), 3.80 (s, 3H); $^{13}$C NMR (125 MHz, CDCl$_3$) δ 160.2, 153.5, 142.8, 130.1, 129.9, 127.0, 125.2, 124.4, 121.7, 121.6, 119.7, 116.4, 114.2, 112.9, 55.6, 53.8; IR (film): 3043, 3009, 2959, 2834, 1610, 1485, 1286, 1227, 788 cm$^{-1}$; HRMS (EI): Mass calculated for [M]$^+$ C$_{16}$H$_{14}$O$_2$: 238.0994; found 238.0983; Enantiomeric ratio was measured by chiral phase HPLC (Chiralcel OJ-H; 100% hexanes; 0.7 mL/min, 280 nm), Rt$_1$ (minor)=102.8, Rt$_2$ (major)=127.3 min; er=94:6.

Example 26

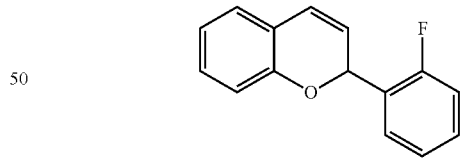

2-(2-Fluorophenyl)-2H-chromene (2g)

Prepared according to the general procedure using 1g. The residue was purified by flash chromatography using 0.8% EtOAc/hexanes to afford 2g as a light yellow oil (61 mg, 75%). Analytical data for 2g: $^1$H NMR (500 MHz, CDCl$_3$) δ7.51 (td, J=7.6, 1.8 Hz, 1H), 7.30 (dddd, J=8.2, 7.2, 5.3, 1.8 Hz, 1H), 7.15-7.11 (m, 2H), 7.08 (ddd, J=10.3, 8.3, 1.2 Hz, 1H), 7.01 (dd, J=7.5, 1.7 Hz, 1H), 6.88 (td, J=7.4, 1.1 Hz, 1H), 6.81 (dt, J=8.1, 1.0 Hz, 1H), 6.54 (ddd, J=9.9, 1.9, 0.8 Hz, 1H), 6.29 (dd, J=3.6, 1.9 Hz, 1H), 5.79 (ddd, J=10.0, 3.6, 1.1 Hz, 1H); $^{13}$C NMR (125 MHz, CDCl$_3$) δ 159.6 (d, J=247.4 Hz), 153.2, 130.0 (d, J=8.2 Hz), 129.7, 128.7 (d, J=3.9 Hz), 128.1 (d, J=13.4 Hz), 126.8, 124.5 (d, J=3.6 Hz), 124.4, 123.8, 121.5, 121.2, 116.1, 115.7 (d, J=21.4 Hz), 71.2 (d, J=3.8 Hz); IR (film): 3044, 2923, 2851, 1641, 1485 cm$^{-1}$; HRMS (EI): Mass calculated for [M]$^+$ C$_{15}$H$_{11}$FO: 226.0794; found: 226.0808; Enantiomerljic ratio was measured by chiral phase HPLC (Chiralcel OJ-H; 100% hexanes; 0.7 mL/min, 280 nm), Rt$_1$ (minor)=22.2, Rt$_2$ (major)=35.3 min; er=91:9.

Example 27

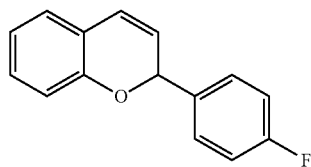 [SMILES: Fc1ccc(C2C=Cc3ccccc3O2)cc1]

2-(4-Fluorophenyl)-2H-chromene (2h)

Prepared according to the general procedure using 1h. The residue was purified by flash chromatography using 1% EtOAc/hexanes to afford 2h as a light yellow oil (69 mg, 84%). Analytical data for 2h: $^1$H NMR (500 MHz, CDCl$_3$) δ7.43 (td, J=5.9, 5.3, 1.9 Hz, 2H), 7.12 (td, J=7.8, 1.7 Hz, 1H), 7.05 (t, J=8.7 Hz, 2H), 7.02 (dd, J=7.5, 1.7 Hz, 1H), 6.88 (td, J=7.4, 1.1 Hz, 1H), 6.77 (d, J=7.9 Hz, 1H), 6.56 (dd, J=9.9, 1.9 Hz, 1H), 5.90 (dd, J=3.5, 1.9 Hz, 1H), 5.78 (dd, J=9.9, 3.4 Hz, 1H); $^{13}$C NMR (125 MHz, CDCl$_3$) δ 162.8 (d, J=246.8 Hz), 153.0, 136.7 (d, J=3.2 Hz), 129.7, 129.1 (d, J=8.3 Hz), 126.8, 124.6, 124.4, 121.44, 121.35, 116.2, 115.7 (d, J=21.5 Hz), 76.5; $^{19}$F NMR (376 MHz, CDCl$_3$) δ –113.75; IR (film): 2922, 2852, 1719, 1603, 1509, 1484, 1457, 1224, 1204 cm$^{-1}$; HRMS (EI): Mass calculated for [M]$^+$ C$_{15}$H$_{11}$FO: 226.0794; found: 226.0764; Enantiomeric ratio was measured by chiral phase HPLC (Whelk-O; 100% hexanes; 1.0 mL/min, 280 nm), Rt$_1$ (minor)=9.5, Rt$_2$ (major)=10.5 min; er=95:5.

Example 28

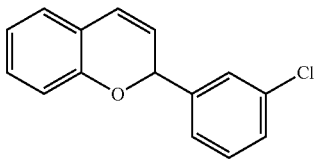 [SMILES: Clc1cccc(C2C=Cc3ccccc3O2)c1]

2-(3-Chlorophenyl)-2H-chromene (2i)

Prepared according to the general procedure using 1i. The residue was purified by flash chromatography using 0.6% EtOAc/hexanes to afford 2i as a light yellow oil (71 mg, 81%). Analytical data for 2i: $^1$H NMR (500 MHz, CDCl$_3$) δ 7.46 (q, J=1.4 Hz, 1H), 7.34 (qd, J=4.3, 1.5 Hz, 1H), 7.32-7.30 (m, 2H), 7.14 (td, J=7.8, 1.7 Hz, 1H), 7.03 (dd, J=7.5, 1.7 Hz, 1H), 6.89 (td, J=7.4, 1.2 Hz, 1H), 6.81 (d, J=8.1 Hz, 1H), 6.56 (dd, J=9.9, 1.9 Hz, 1H), 5.90 (dd, J=3.5, 1.9 Hz, 1H), 5.78 (dd, J=9.9, 3.4 Hz, 1H); $^{13}$C NMR (125 MHz, CDCl$_3$) δ 152.9, 142.9, 134.6, 130.1, 129.8, 128.6, 127.3, 126.8, 125.2, 124.6, 124.1, 121.6, 121.2, 116.1, 76.4; IR (film): 3048, 2923, 2847, 1638, 1602, 1574, 1483, 1457, 1430, 1349 cm$^{-1}$; HRMS (EI): Mass calculated for [M]$^+$ C$_{15}$H$_{11}$ClO: 242.0498; found: 242.0508; Enantiomeric ratio was measured by chiral phase HPLC (Whelk-O; 100% hexanes; 0.35 mL/min, 280 nm), Rt$_1$ (minor)=27.0, Rt$_2$ (major)=31.7 min; er=93:7.

Example 29

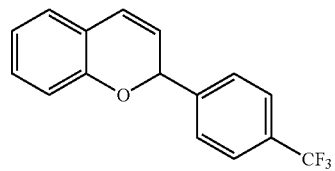 [SMILES: FC(F)(F)c1ccc(C2C=Cc3ccccc3O2)cc1]

2-(4-(Trifluoromethyl)phenyl)-2H-chromene (2j)

Prepared according to the general procedure using 1j. The residue was purified by flash chromatography using 1% EtOAc/hexanes to afford 2j as a light yellow oil (66 mg, 84%). Analytical data for 2j: $^1$H NMR (500 MHz, CDCl$_3$) δ 7.63 (d, J=8.1 Hz, 2H), 7.57 (d, J=8.1 Hz, 2H), 7.14 (td, J=7.8, 1.6 Hz, 1H), 7.02 (dd, J=7.4, 1.6 Hz, 1H), 6.89 (td, J=7.5, 1.1 Hz, 1H), 6.81 (d, J=8.0 Hz, 1H), 6.57 (dd, J=9.8, 1.8 Hz, 1H), 5.97 (s, 1H), 5.79 (dd, J=9.8, 3.5 Hz, 1H); $^{13}$C NMR (125 MHz, CDCl$_3$) δ 152.9, 144.8, 130.5 (d, J=32.4 Hz), 129.9, 127.3, 126.9, 125.8 (q, J=3.8 Hz), 124.7, 124.1 (d, J=272.0 Hz), 124.0, 121.7, 121.2, 116.1, 76.4; $^{9}$F NMR (376 MHz, CDCl$_3$) δ –62.64; IR (film): 3047, 2925, 2854, 1620, 1574, 1485, 1457, 1418, 1325 cm$^{-1}$; HRMS (EI): Mass calculated for [M]$^+$ C$_{16}$H$_{11}$F$_3$O: 276.0762; found: 276.0736; Enantiomeric ratio was measured by chiral phase HPLC (Chiralcel OJ-H; 100% hexanes; 0.7 mL/min, 280 nm), Rt$_1$ (minor)=30.8, Rt$_2$ (major)=44.4 min; er=83:17.

Example 30

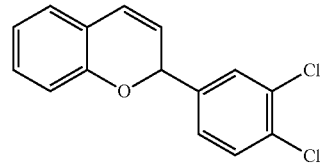 [SMILES: Clc1ccc(C2C=Cc3ccccc3O2)cc1Cl]

2-(3,4-Dichlorophenyl)-2H-chromene (2k)

Prepared according to the general procedure using 1k. The residue was purified by flash chromatography using 1% EtOAc/hexanes to afford 2k as a light yellow oil (74 mg, 74%). Analytical data for 2k: $^1$H NMR (500 MHz, CDCl$_3$) δ 7.54 (d, J=2.1 Hz, 1H), 7.43 (d, J=8.3 Hz, 1H), 7.29 (dd, J=8.3, 2.1 Hz, 1H), 7.13 (td, J=7.8, 1.7 Hz, 1H), 7.02 (dd, J=7.5, 1.7 Hz, 1H), 6.89 (td, J=7.5, 1.1 Hz, 1H), 6.79 (dt, J=8.0, 0.9 Hz, 1H), 6.57 (dd, J=9.7, 1.4 Hz, 1H), 5.87 (dd, J=3.6, 1.8 Hz, 1H), 5.76 (dd, J=9.8, 3.5 Hz, 1H); $^{13}$C NMR (125 MHz, CDCl$_3$) δ 153.0, 141.3, 133.1, 132.7, 131.0, 130.2, 129.5, 127.2, 126.7, 125.2, 123.9, 122.0, 121.4, 116.4, 76.0; IR (film): 3076, 2924, 2827, 1641, 1486 cm$^{-1}$; HRMS (EI): Mass calculated for [M]$^+$ C$_{15}$H$_{10}$C$_{12}$O: 276.0109; found: 276.0137; Enantiomeric ratio was measured by chiral phase HPLC (Chiralcel OJ-H; 100% hexanes; 0.5 mL/min, 280 nm), Rt$_1$ (major)=78.0, Rt$_2$ (minor)=133.5 min; er=90:10.

Example 31

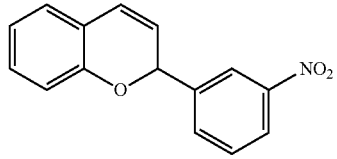 [SMILES: O=[N+]([O-])c1cccc(C2C=Cc3ccccc3O2)c1]

2-(3-Nitrophenyl)-2H-chromene (2l)

Prepared according to the general procedure using 1l. The residue was purified by flash chromatography using 1% EtOAc/hexanes to afford 2l as a light yellow oil (65 mg, 71%). Analytical data for 2l: $^1$H NMR (500 MHz, CDCl$_3$) δ 8.32 (q, J=1.9 Hz, 1H), 8.18 (ddt, J=8.4, 2.6, 1.3 Hz, 1H), 7.81 (dt, J=7.8, 1.5 Hz, 1H), 7.55 (td, J=8.0, 1.8 Hz, 1H), 7.15 (tt, J=7.6, 1.7 Hz, 1H), 7.04 (dt, J=7.6, 1.8 Hz, 1H), 6.90 (tt, J=7.5, 1.4 Hz, 1H), 6.82 (d, J=8.1 Hz, 1H), 6.62 (dt, J=10.0, 1.9 Hz, 1H), 6.02 (dd, J=3.7, 1.9 Hz, 1H), 5.83 (ddd, J=9.8, 3.6, 1.7 Hz, 1H); $^{13}$C NMR (125 MHz, CDCl$_3$) δ 152.7, 148.5, 143.0, 133.2, 130.0, 129.8, 127.0, 125.3, 123.4, 123.3, 122.1, 121.9, 121.2, 116.2, 75.7; IR (film): 3065, 3032, 2920, 2845, 1645, 1612, 1587, 1500, 1454, 1432, 1264, 1160, 1138, 1105, 1036, 982 cm$^{-1}$; HRMS (EI): Mass calculated for [M]$^+$ C$_{15}$H$_{11}$NO$_3$: 253.0739; found: 253.0715; Enantiomeric ratio was measured by chiral phase HPLC (Whelk-O; 100% hexanes; 0.2 mL/min, 280 nm), Rt$_1$ (minor)=48.0, Rt$_2$ (major)=51.8 min; er=92:8.

Example 32

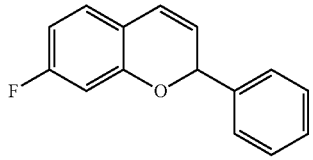 [SMILES: Fc1ccc2c(c1)OC(c1ccccc1)C=C2]

7-Fluoro-2-phenyl-2H-chromene (2m)

Prepared according to the general procedure using 1m. The residue was purified by flash chromatography using 0.5% EtOAc/hexanes to afford 2m as a light yellow oil (56 mg, 69%). Analytical data for 2m: $^1$H NMR (500 MHz, CDCl$_3$) δ 7.45-7.32 (m, 5H), 6.96 (dd, J=8.3, 6.4 Hz, 1H), 6.57 (td, J=8.4, 2.5 Hz, 1H), 6.51 (ddd, J=10.0, 3.7, 2.1 Hz, 2H), 5.91 (q, J=3.1, 1.9 Hz, 1H), 5.76 (dd, J=9.9, 3.4 Hz, 1H); $^{13}$C NMR (125 MHz, CDCl$_3$) δ 163.4 (d, J=246.7 Hz), 154.5 (d, J=12.4 Hz), 140.5, 128.9, 128.7, 127.55 (d, J=10.0 Hz), 127.2, 123.6 (d, J=2.6 Hz), 123.3, 117.7 (d, J=3.2 Hz), 108.0 (d, J=21.9 Hz), 104.1 (d, J=25.1 Hz), 77.4; IR (film): 3065, 3032, 2920, 2845, 1645, 1612, 1587, 1500, 1454, 1432, 1264, 1160, 1137, 1105, 1036, 982, 852 cm$^{-1}$; HRMS (EI): Mass calculated for [M]$^+$ C$_{15}$H$_{11}$FO: 226.0794; found: 226.0804; Enantiomeric ratio was measured by chiral phase HPLC (Whelk-O; 100% hexanes; 0.2 mL/min, 280 nm), Rt$_1$ (minor)=45.9, Rt$_2$ (major)=52.6 min; er=90:10.

Example 33

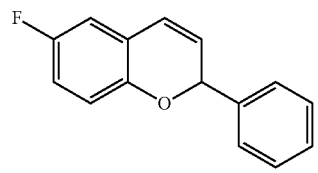 [SMILES: Fc1ccc2c(c1)C=CC(c1ccccc1)O2]

6-Fluoro-2-phenyl-2H-chromene (2n)

Prepared according to the general procedure using 1n. The residue was purified by flash chromatography using 0.5% EtOAc/hexanes to afford 2n as white solids (59 mg, 72%). Analytical data for 2n: $^1$H NMR (500 MHz, CDCl$_3$) δ 7.43 (dt, J=6.9, 2.1, 1.6 Hz, 2H), 7.40-7.31 (m, 3H), 6.79 (td, J=8.5, 3.0 Hz, 1H), 6.76-6.69 (m, 2H), 6.49 (dt, J=7.7, 3.1, 2.6 Hz, 1H), 5.91-5.85 (m, 2H); $^{13}$C NMR (125 MHz, CDCl$_3$) δ 157.4 (d, J=238.3 Hz), 149.1 (d, J=1.8 Hz), 140.3, 128.7, 128.6, 127.1, 126.4, 123.6 (d, J=2.1 Hz), 122.3 (d, J=8.4 Hz), 116.9 (d, J=8.1 Hz), 115.5 (d, J=23.2 Hz), 112.8 (d, J=23.8 Hz), 77.2; $^9$F NMR (376 MHz, CDCl$_3$) δ −123.28; IR (film): 3063, 3032, 2954, 2921, 2851, 1639, 1582, 1485, 1455, 1441, 1371 cm$^{-1}$; HRMS (EI): Mass calculated for [M]$^+$ C$_{15}$H$_{11}$FO: 226.0794; found: 226.0798; Enantiomeric ratio was measured by chiral phase HPLC (Chiralcel OJ-H; 100% hexanes; 0.7 mL/min, 280 nm), Rt$_1$ (minor)=66.2, Rt$_2$ (major)=77.0 min; er=97:3.

Example 34

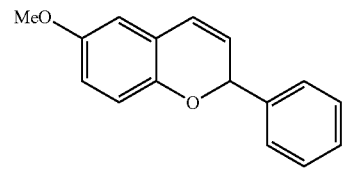 [SMILES: COc1ccc2c(c1)C=CC(c1ccccc1)O2]

6-Methoxy-2-phenyl-2H-chromene (2o)

Prepared according to the general procedure using 1o. The residue was purified by flash chromatography using 1% EtOAc/hexanes to afford 2o as a light yellow oil (68 mg, 80%). Analytical data for 2o: $^1$H NMR (500 MHz, CDCl$_3$) δ 7.47-7.42 (m, 2H), 7.40-7.29 (m, 3H), 6.73 (d, J=8.8 Hz, 1H), 6.67 (ddd, J=8.9, 3.1, 1.2 Hz, 1H), 6.59 (dd, J=3.2, 1.2 Hz, 1H), 6.54-6.46 (m, 1H), 5.88-5.82 (m, 2H), 3.76 (d, J=1.4 Hz, 3H); $^{13}$C NMR (125 MHz, CDCl$_3$) δ 154.1, 147.1, 140.8, 128.8, 128.5, 127.2, 126.0, 124.3, 122.2, 116.7, 114.6, 111.9, 77.1, 55.9; IR (film): 3033, 2998, 2915, 2831, 1609, 1576, 1490, 1429, 1344, 1307, 1265, 1208, 1158, 1117, 1045 cm$^{-1}$; HRMS (EI): Mass calculated for [M]$^+$ C$_{16}$H$_{14}$O$_2$: 238.0994; found 238.0970; Enantiomeric ratio

Example 35

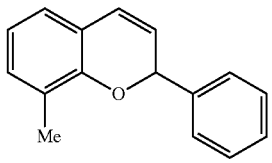 [SMILES: Cc1cccc2c1OC(c1ccccc1)C=C2]

8-Methyl-2-phenyl-2H-chromene (2p)

Prepared according to the general procedure using 1p. The residue was purified by flash chromatography using 0.1% EtOAc/hexanes to afford 2p as a light yellow oil (58 mg, 73%). Analytical data for 2p: $^1$H NMR (500 MHz, CDCl$_3$) δ 7.45 (d, J=7.5 Hz, 2H), 7.39-7.29 (m, 3H), 6.98 (d, J=7.5 Hz, 1H), 6.86 (d, J=7.5 Hz, 1H), 6.77 (t, J=7.5 Hz, 1H), 6.52 (dd, J=9.9, 1.8 Hz, 1H), 5.94 (dd, J=3.7, 1.8 Hz, 1H), 5.82 (dd, J=9.8, 3.6 Hz, 1H), 2.16 (s, 3H); $^{13}$C NMR (125 MHz, CDCl$_3$) δ 151.5, 141.6, 131.3, 128.9 (2C), 128.5, 127.1 (2C), 125.6, 124.9, 124.7 (2C), 121.3, 120.9, 77.0, 16.0; IR (film): 3062, 3044, 3029, 2920, 2851, 1644, 1602, 1494, 1455, 1390, 1344, 1304, 1264, 1208, 1178, 1156, 1082, 1055, 1029, 1001, 968, 939, 917 cm$^{-1}$; HRMS (EI): Mass calculated for [M]$^+$ C$_{16}$H$_{14}$O: 222.1045; found 222.1031; Enantiomeric ratio was measured by chiral phase HPLC (Chiralcel OJ-H; 5% IPA/hexanes; 1.0 mL/min, 280 nm), Rt$_1$ (minor)=8.7, Rt$_2$ (major)=12.5 min; er=85:15.

Example 36

General Procedure for Racemic Synthesis of Chromenes

To a round bottom flask equipped with magnetic stir bar was dissolved 2'-hydroxychalcone derivative (0.5 mmol, 1 equiv) in isopropanol (5 mL). Mixture was heated to 70° C. before NaBH$_4$ (1.5 mmol, 3 equiv.) was added in one portion and was slowly cooled to 23° C. Ice was added and the resulting solution was acidified using 10% glacial acetic acid to pH 5. The solution was extracted with CH$_2$Cl$_2$, organics washed with brine, dried over sodium sulfate, filtered, and concentrated under reduced pressure. The residue was purified by flash chromatography with EtOAc/hexanes to afford the corresponding chromenes.

Ligand Synthesis

Example 37

To a solution of diol (2.94 mmol, 1 equiv) and triethylamine (14.68 mmol, 5 equiv) in dry, oxygen-free THF (18 mL) at 0° C. was added PCl$_3$ (3.52 mmol, 1.2 equiv). After stirring for 2 h at 23° C. under positive N$_2$ pressure, reaction was cooled to 0° C. before a solution of piperidine (5.87 mmol, 2 equiv) in dry, oxygen-free THF (10 mL) was slowly added via cannula. The resulting mixture was slowly warmed to 23° C. and stirred for 20 h under positive N$_2$ pressure. Reaction was diluted with Et$_2$O, filtered through a plug of Celite®, and concentrated under reduced pressure. The residue was purified by flash chromatography using EtOAc/hexanes to afford the corresponding phosphoramidites.

Example 38

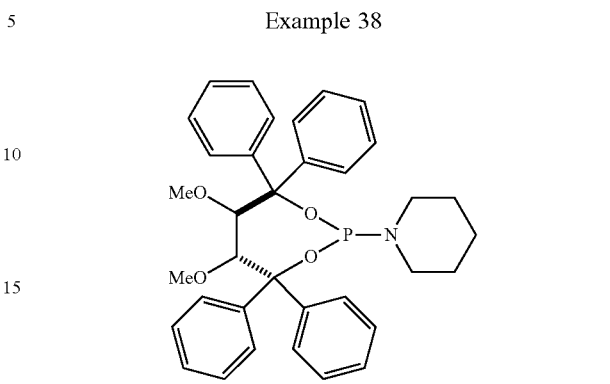

1-((5R,6R)-5,6-Dimethoxy-4,4,7,7-tetraphenyl-1,3,2-dioxaphosphepan-2-yl)piperidine (L4)

Prepared according to the general procedure using (2R,3R)-2,3-dimethoxy-1,1,4,4-tetraphenylbutane-1,4-diol. The residue was purified by flash chromatography using 1% EtOAc/hexanes to afford L4 as a white foam (44 mg, 65%). Analytical data for L4: $^1$H NMR (500 MHz, CDCl$_3$) δ 7.73 (d, J=7.0 Hz, 2H), 7.53 (d, J=7.3 Hz, 2H), 7.43 (d, J=7.2 Hz, 2H), 7.36-7.18 (m, 14H), 4.50 (dd, J=7.3, 3.6 Hz, 1H), 4.30 (d, J=7.3 Hz, 1H), 3.26 (s, 3H), 3.16 (dtd, J=15.1, 7.0, 3.1 Hz, 2H), 2.83 (m, 2H), 2.58 (s, 3H), 1.54-1.37 (m, 6H); $^{13}$C NMR (126 MHz, CDCl$_3$) δ 146.6, 146.5, 142.3, 141.92, 141.89, 129.10, 129.08, 128.7, 128.0, 127.6, 127.43, 127.39, 127.3, 127.24, 127.22, 126.88, 126.85, 126.8, 84.74, 84.69, 83.7, 82.4, 82.3, 81.0, 80.9, 59.7, 59.4, 45.1, 44.9, 26.94, 26.91, 25.1; $^{31}$P NMR (162 MHz, CDCl$_3$) δ 133.2; IR (film): 3089, 3057, 3034, 3024, 2932, 2848, 2831, 1599, 1582, 1492, 1445, 1372, 1334, 1316, 1265, 1213, 1184.22 1128, 1041, 974, 947, 805 cm$^{-1}$; LRMS (ESI): Mass calculated for [M+H]$^+$ C$_{35}$H$_{39}$NO$_4$P: 568.3; found 568.4.

Example 39

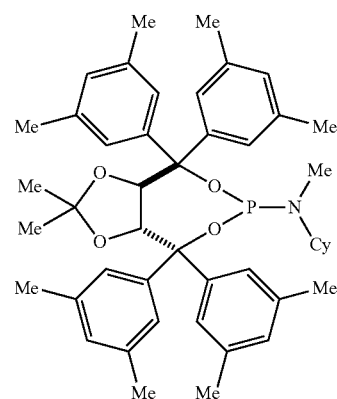

(3aR,8aR)—N-cyclohexyl-4,4,8,8-tetrakis(3,5-dimethylphenyl)-N,2,2-trimethyltetrahydro-[1,3]dioxolo[4,5-e][1,3,2]dioxaphosphepin-6-amine (L3j)

Prepared according to the general procedure using ((4R,5R)-2,2-dimethyl-1,3-dioxolane-4,5-diyl)bis(bis(3,5-dimethylphenyl)methanol). The residue was purified by flash chromatography using 1% EtOAc/hexanes to afford L3j as a white foam (195 mg, 77%). Analytical data for L3j: $^1$H NMR (500 MHz, CDCl$_3$) δ 7.45 (s, 2H), 7.21 (s, 2H), 7.06 (d, J=10.2 Hz, 4H), 6.88-6.78 (m, 4H), 5.07 (dd, J=8.5, 3.5 Hz, 1H), 4.65 (d, J=8.5 Hz, 1H), 3.25 (tdd, J=11.8, 8.2, 3.4 Hz, 1H), 2.81 (d, J=7.6 Hz, 3H), 2.29 (s, 6H), 2.27 (s, 6H), 2.26 (s, 12H), 1.88-1.70 (m, 4H), 1.60 (d, J=14.4 Hz, 1H), 1.54-1.47 (m, 2H), 1.45 (s, 3H), 1.27 (ddt, J=20.8, 12.7, 3.6 Hz, 2H), 1.05 (ddd, J=16.6, 8.4, 3.5 Hz, 1H), 0.22 (s, 3H); $^{13}$C NMR (126 MHz, CDCl$_3$) δ 147.5, 147.04, 147.02, 142.3, 142.1, 137.1, 136.8, 136.7, 136.3, 129.0, 128.9, 128.8, 128.7, 127.1, 126.64, 126.61, 125.2, 111.2, 83.61, 83.59, 83.0, 82.8, 81.2, 81.1, 80.72, 80.70, 57.5, 57.2, 32.60, 32.55, 32.5, 32.4, 27.9, 27.6, 27.5, 26.50, 26.48, 25.9, 25.4, 21.84, 21.78, 21.7; $^{31}$P NMR (162 MHz, CDCl$_3$) δ 140.0; IR (film): 3047, 2990, 2930, 2855, 2731, 1787, 1754, 1600, 1450, 1380, 1265, 1214, 1159, 1066, 969, 942, 861, 785, 738, 690, 601, 574, 508, 413 cm$^{-1}$; LRMS (ESI): Mass calculated for [M+H]$^+$ C$_{46}$H$_{59}$NO$_4$P: 720.4; found 720.6.

Example 40

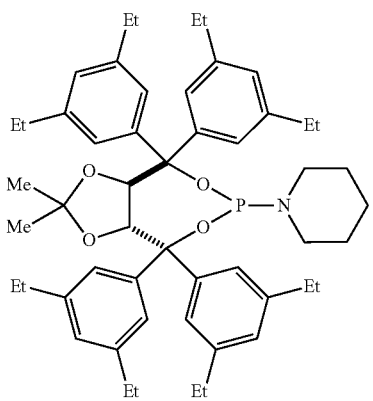

1-((3aR,8aR)-4,4,8,8-Tetrakis(3,5-diethylphenyl)-2,2-dimethyltetrahydro-[1,3]dioxolo[4,5-e][1,3,2]dioxaphosphepin-6-yl)piperidine (L3k)

Prepared according to the general procedure using ((4R,5R)-2,2-dimethyl-1,3-dioxolane-4,5-diyl)bis(bis(3,5-diethylphenyl)methanol). The residue was purified by flash chromatography using 1% EtOAc/hexanes to afford L3k as a white foam (2.15 g, 91%). Analytical data for L3k: $^1$H NMR (500 MHz, CDCl$_3$) δ 7.45 (d, J=1.6 Hz, 2H), 7.30 (d, J=1.6 Hz, 2H), 7.13 (s, 2H), 7.05 (d, J=1.6 Hz, 2H), 6.92-6.82 (m, 4H), 5.15 (dd, J=8.5, 3.1 Hz, 1H), 4.78 (d, J=8.5 Hz, 1H), 3.38-3.26 (m, 2H), 3.16 (ddd, J=15.0, 8.8, 5.4 Hz, 2H), 2.66-2.51 (m, 16H), 1.65-1.51 (m, 6H) 1.36 (s, 3H), 1.19 (dtt, J=7.1, 4.3, 2.1 Hz, 24H), 0.18 (s, 3H); $^{13}$C NMR (125 MHz, CDCl$_3$) δ 147.2, 146.9, 143.4, 142.9, 142.5, 142.1, 142.0, 126.3, 126.2, 126.2, 126.04, 125.99, 125.96, 124.4, 124.3, 110.9, 83.33, 83.31, 82.8, 82.7, 81.6, 81.5, 81.3, 45.1, 44.9, 29.1, 29.0, 28.93, 28.91, 27.7, 27.2, 27.1, 25.3, 25.1, 15.9, 15.6, 15.4; $^{31}$P NMR (162 MHz, CDCl$_3$) δ 137.2; IR (film): 2964, 2933, 2873, 1600, 1459, 1371, 1333, 1247, 1215, 1160, 1072, 1038, 949, 875, 853, 783, 739, 703, 506, 432, 411 cm$^{-1}$; LRMS (ESI): Mass calculated for [M+H]$^+$ C$_{52}$H$_{71}$NO$_4$P: 804.5; found 804.5.

Example 41

Synthesis of [Pd(η$^3$-1,3-diphenylallyl){(S,S)-L3g}]BF$_4$

Bis[(μ-chloro)(η$^3$-1,3-diphenylallyl)palladium(II)]

Prepared according to procedure described by Pregosin and co-workers. (P. Barbaro, A. Currao, J. Herrmann, R. Nesper, P. S. Pregosin, and R. Salzmann, *Organometallics*, 1996, 15, 1879-1888.) PdCl$_2$ (350 mg, 1.95 mmol) and LiCl (350 mg, 8.3 mmol) were stirred in H$_2$O (2.3 mL) for 45 min. Ethanol (3.9 mL) and (rac)-(E)-3-acetoxy-1,3-diphenyl-1-propene (1 g, 3.97 mmol) in THF (11 mL) were then added, and the brown solution was cooled to 0° C. After the addition of 1.2 mL of concentrated HCl, carbon monoxide was slowly bubbled through the solution for 15 min. Another 0.8 mL of concentrated HCl was added and CO bubbled for 1.5 h. The stream of CO was then stopped and the solution stirred under CO atmosphere for 7 h at 23° C. The yellow mixture was filtered, washed with MeOH and Et$_2$O, and dried under vacuum overnight. Spectroscopic data was consistent with those previously reported.

Example 42

[Pd(η$^3$-1,3-diphenylallyl){(S,S)-L3g)]}BF$_4$

To a solution of bis[(μ-chloro)(η$^3$-1,3-diphenylallyl)palladium(II)] (12 mg, 0.018 mmol) in anhydrous acetone was added (S,S)-L3g (25 mg, 0.035 mmol). The mixture was stirred for 2 h at 23° C. To the yellow solution was added a solution of silver tetrafluoroborate (7.59 mg, 0.039 mmol) in THF. The filtrate was concentrated at reduced pressure, and CH$_2$Cl$_2$ was added. Pentane was carefully layered on top to induce crystallization and afford [Pd(η$^3$-1,3-diphenylallyl){(S,S)-L3g}]BF$_4$ as yellow needles.

Synthetic Transformations

Example 43

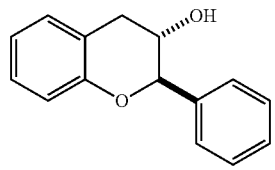 [SMILES: O[C@H]1Cc2ccccc2O[C@@H]1c1ccccc1]

(2R,3S)-2-Phenylchroman-3-ol (7)

A solution of 2-phenyl-2H-chromene (2a) (167 mg, 0.8 mmol) and 1 molar BH$_3$-THF (16 mL) was stirred for 2 h at 23° C. Solution was cooled to 0° C. before a 20% (w/w) aqueous solution of NaOH (4.8 mL) and 30% (w/w) aqueous solution of H$_2$O$_2$ (4.9 mL) were added. The reaction was slowly warmed to 23° C. and stirred for 12 h. The solution was then diluted with Et$_2$O and H$_2$O followed by acidification with 10% (w/w) aqueous HCl and extraction with Et$_2$O. The organics were combined, dried over magnesium sulfate, filtered, and concentrated under reduced pressure. Purification by flash chromatography with 10% EtOAc/hexanes afforded 7 as a white solid (115 mg, 63%). Spectroscopic data was consistent with those previously reported.

Example 44

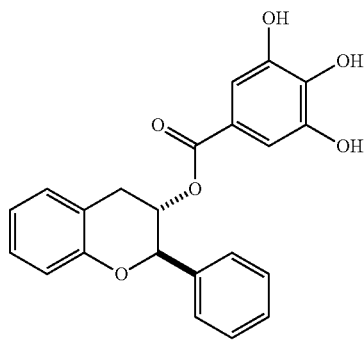 [SMILES: O=C(O[C@H]1Cc2ccccc2O[C@@H]1c1ccccc1)c1cc(O)c(O)c(O)c1]

(2R,3S)-2-Phenylchroman-3-yl 3,4,5-trihydroxybenzoate (8)

Prepared using a modified literature procedure. (J. C. Anderson, R. A. McCarthy, S. Paulin and P. W. Taylor, *Bioorg. Med. Chem. Lett.*, 2011, 21, 6996-7000.) To a solution of (2R,3S)-2-phenylchroman-3-ol (7) (91 mg, 0.4 mmol) in $CH_2Cl_2$ (2 mL) was added DMAP (28 mg, 0.23 mmol), $Et_3N$ (0.167 mL, 1.2 mmol) and tri-OBn gallic acid chloride (184 mg, 0.4 mmol). The reaction was stirred for 12 h at 23° C., washed with $H_2O$ followed by brine, dried over magnesium sulfate, filtered, and concentrated under reduced pressure. The protected gallate ester was taken up in EtOAc (4 mL). To the solution was added 10 wt. % Pd/C (255 mg, 2.4 mmol). The mixture was stirred under an atmosphere of $H_2$ for 14 h, filtered through a plug of Celite®, dried over sodium sulfate, filtered, and concentrated under reduced pressure. Purification by flash chromatography with 30% EtOAc/hexanes afforded 8 as a white solid (89 mg, 59%). Analytical data for 8: $^1$H NMR (500 MHz, $CDCl_3$) δ 7.40 (dd, J=7.5, 1.8 Hz, 2H), 7.34 (t, J=7.4 Hz, 2H), 7.29 (d, J=7.2 Hz, 1H), 7.21 (td, J=7.8, 7.4, 1.7 Hz, 1H), 7.10 (s, 2H), 7.09-7.05 (m, 1H), 7.01 (dd, J=8.2, 1.2 Hz, 1H), 6.93 (td, J=7.4, 1.2 Hz, 1H), 5.70 (bs, 1H), 5.55 (td, J=6.0, 4.9 Hz, 1H), 5.46 (bs, 2H), 5.33 (d, J=5.7 Hz, 1H), 3.11 (dd, J=16.7, 4.8 Hz, 1H), 2.96 (dd, J=16.6, 6.1 Hz, 1H); $^{13}$C NMR (125 MHz, $CDCl_3$) δ 143.1, 138.2, 129.8, 128.6, 128.3, 127.9, 126.2, 121.0, 116.5, 109.9, 78.4, 69.9, 28.6. Other spectroscopic data was consistent with those previously reported.

Example 45

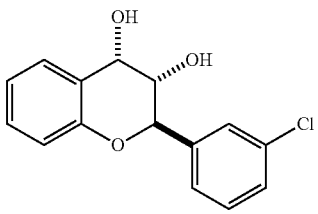 [SMILES: O[C@@H]1[C@@H](c2cccc(Cl)c2)Oc2ccccc2[C@@H]1O]

(2R,3S,4S)-2-(3-Chlorophenyl)chromane-3,4-diol (9)

To a solution of 2-(3-chlorophenyl)-2H-chromene (2i) (72.8 mg, 0.3 mmol) and 4-methylmorpholine N-oxide (52.7 mg, 0.45 mmol) in THF (3 mL) and water (0.116 mL) was added a 2.5 wt % solution of osmium tetraoxide in t-BuOH (0.118 mL). The mixture was stirred at 23 C for 16 h and was then quenched with a saturated solution of sodium thiosulfate. The mixture was extracted with EtOAc. The combined organics was washed with brine, dried over sodium sulfate, filtered, and concentrated under reduced pressure. The crude was purified by flash chromatography using 20% EtOAc/hexanes to afford 9 as an off-white solid (76 mg, 91%). Analytical data for 9: $^1$H NMR (500 MHz, $CDCl_3$) δ 7.53-7.48 (m, 1H), 7.39 (dd, J=7.6, 1.7 Hz, 1H), 7.37 (d, J=1.4 Hz, 3H), 7.30 (ddd, J=8.6, 7.3, 1.7 Hz, 1H), 7.02 (td, J=7.4, 1.2 Hz, 1H), 6.96 (dd, J=8.2, 1.1 Hz, 1H), 5.05 (d, J=9.5 Hz, 1H), 4.81 (t, J=3.7 Hz, 1H), 4.04 (ddd, J=9.5, 6.6, 3.7 Hz, 1H), 2.57 (d, J=3.7 Hz, 1H), 2.25 (d, J=6.6 Hz, 1H); $^{13}$C NMR (125 MHz, $CDCl_3$) δ 154.0, 139.9, 134.8, 130.9, 130.7, 130.1, 129.0, 127.8, 125.9, 122.0, 121.7, 117.0, 76.2, 71.1, 66.2; IR (film): 3407, 2919, 2851, 1583, 1485, 1455, 1239, 1036, 1012, 754, 701, 511 $cm^{-1}$; LRMS (ESI): Mass calculated for $[M+H]^+$ $C_{15}H_{14}ClO_3$: 277.1; found 277.1.

Example 46

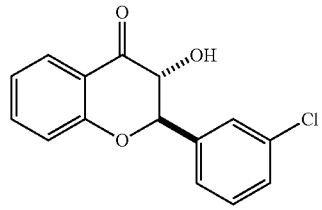 [SMILES: O=C1c2ccccc2O[C@H](c2cccc(Cl)c2)[C@H]1O]

(2R,3R)-2-(3-Chlorophenyl)-3-hydroxychroman-4-one (10)

To a solution of (2R,3S,4S)-2-(3-chlorophenyl)chromane-3,4-diol (9) (28 mg, 0.1 mmol) in $CH_2Cl_2$ (2 mL) was added manganese dioxide (44 mg, 0.5 mmol). The mixture was stirred at 23° C. for 24 h, filtered through a plug of Celite®, and concentrated under reduced pressure. The crude was purified by flash chromatography using 7% EtOAc/hexanes to afford 10 as a solid (16 mg, 59%). Analytical data for 9: $^1$H NMR (500 MHz, $CDCl_3$) δ 7.93 (dd, J=7.9, 1.7 Hz, 1H), 7.62 (d, J=2.0 Hz, 1H), 7.58 (ddd, J=8.6, 7.2, 1.8 Hz, 1H), 7.48-7.45 (m, 1H), 7.42-7.38 (m, 2H), 7.14 (ddd, J=8.0, 7.2, 1.0 Hz, 1H), 7.07 (dd, J=8.4, 1.0 Hz, 1H), 5.12 (d, J=12.3 Hz, 1H), 4.57 (dd, J=12.3, 1.9 Hz, 1H), 3.70 (d, J=1.9 Hz, 1H); $^{13}$C NMR (125 MHz, $CDCl_3$) δ 193.8, 161.5, 138.3, 137.1, 134.6, 129.9, 129.4, 127.6, 127.4, 125.8, 122.4, 118.4, 118.1, 83.0, 73.6; IR (film): 3461, 2921, 2851, 2361, 2341, 1695, 1608, 1579, 1466, 1300, 1229, 1138, 1104, 1009, 861, 764, 693, 419, 405 $cm^{-1}$; LRMS (ESI): Mass calculated for $[M+H]^+$ $C_{15}H_{12}ClO_3$: 275.0; found 275.1.

While the principles of this invention have been described in connection with certain embodiments, it should be understood clearly that these descriptions are provided only by way of example and are not intended to limit, in any way, the scope of this invention. For instance, the present invention can be applied to arylallyl-substituted phenoxy ester starting materials where R can be one or more $C_1$-$C_6$ alkyl and/or alkoxy moieties and Ar can be substituted with one or more $C_1$-$C_6$ alkyl and/or alkoxy moieties to provide corresponding 2-aryl chromene compounds. Other advantages and features of this invention will become apparent from the claims hereinafter, with the scope of such claims determined by the reasonable equivalents as would be understood by those skilled in the art.

We claim:

1. A composition comprising compounds of a formula

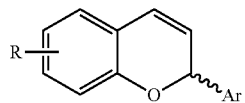

wherein R is selected from H, halo, alkyl and alkoxy moieties and Ar is selected from phenyl and substituted phenyl moieties, said phenyl substituents selected from halo, alkyl, alkoxy, nitro and haloalkyl substituents, multiple said substituents and combinations thereof, said composition comprising at least about 70% an enantiomer of a formula

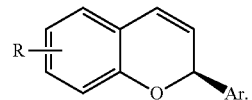

2. The composition of claim 1 wherein said phenyl moiety is selected from methyl, a methoxy, fluoro, chloro, nitro and dichloro substituted phenyl moieties, said composition comprising at least about 90% said enantiomer.

* * * * *